(12) United States Patent
Bovet et al.

(10) Patent No.: US 10,501,732 B2
(45) Date of Patent: Dec. 10, 2019

(54) THREONINE SYNTHASE FROM NICOTIANA TABACUM AND METHODS AND USES THEREOF

(75) Inventors: Lucien Bovet, La Chaux-de-Fonds (CH); Nicolas Sierro, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 14/241,189

(22) PCT Filed: Aug. 31, 2012

(86) PCT No.: PCT/EP2012/003663
§ 371 (c)(1),
(2), (4) Date: Apr. 11, 2014

(87) PCT Pub. No.: WO2013/029800
PCT Pub. Date: Mar. 7, 2013

(65) Prior Publication Data
US 2015/0106971 A1    Apr. 16, 2015

(30) Foreign Application Priority Data
Sep. 2, 2011   (EP) .................................. 11179889

(51) Int. Cl.
| C12N 9/88 | (2006.01) |
| C12N 15/82 | (2006.01) |
| A24B 13/00 | (2006.01) |
| C07C 381/00 | (2006.01) |
| C12Q 1/6895 | (2018.01) |

(52) U.S. Cl.
CPC .............. *C12N 9/88* (2013.01); *A24B 13/00* (2013.01); *C07C 381/00* (2013.01); *C12N 15/8253* (2013.01); *C12Q 1/6895* (2013.01); *C12Q 2600/13* (2013.01); *C12Q 2600/16* (2013.01); *C12Y 402/03001* (2013.01)

(58) Field of Classification Search
CPC ... C12N 15/82; C12N 9/88; C12Y 402/03001
See application file for complete search history.

(56) References Cited

U.S. PATENT DOCUMENTS

| 7,323,338 B2 * | 1/2008 | Amir .................... C12N 9/1085 435/468 |
| 2006/0041949 A1 * | 2/2006 | Xu ........................ C07K 14/415 800/278 |
| 2007/0199097 A1 * | 8/2007 | Xu ........................ C12N 9/0073 800/278 |

FOREIGN PATENT DOCUMENTS

| AU | 2012301350 | 3/2017 | |
| EP | WO0175130 A1 * | 10/2001 | ............ C12N 15/82 |
| WO | WO 98/55601 | 12/1998 | |
| WO | WO 00/55303 | 9/2000 | |
| WO | WO0055303 A1 * | 9/2000 | ............ C12N 15/82 |
| WO | WO 01/75130 | 10/2001 | |
| WO | WO 2009/074325 | 6/2009 | |

OTHER PUBLICATIONS

Zeh, Michaela, et al. "Antisense inhibition of threonine synthase leads to high methionine content in transgenic potato plants." Plant Physiology 127.3 (2001): 792-802.*
Bartlem, Derek, et al. "Mutation in the threonine synthase gene results in an over-accumulation of soluble methionine in Arabidopsis." Plant Physiology 123.1 (2000): 101-110.*
Suzuki, Kenji, Ichiro Yamashita, and Nobukazu Tanaka. "Tobacco plants were transformed by Agrobacterium rhizogenes infection during their evolution." The Plant Journal 32.5 (2002): 775-787.*
EST CK294680, publically available since Aug. 2, 2004, retrieved from NCBI Genbank www.ncbi.nlm.nih.gov/nucest/39878308?report=genbank.*
Friedberg, I. "Automated protein function prediction—the genomic challenge." Briefings in bioinformatics 7.3 (2006): 225-242.*
Hacham, Yael, et al. "Lysine enhances methionine content by modulating the expression of S-adenosylmethionine synthase." The Plant Journal 51.5 (2007): 850-861. (Year: 2007).*
Di, Rong, et al. "Enhancement of the primary flavor compound methional in potato by increasing the level of soluble methionine." Journal of agricultural and food chemistry 51.19 (2003): 5695-5702 (Year: 2003).*
Levin, Joshua Z., et al. "Methods of double-stranded RNA-mediated gene inactivation in *Arabidopsis* and their use to define an essential gene in methionine biosynthesis." Plant molecular biology 44.6 (2000): 759-775. (Year: 2000).*
Stedman, Russell L. "Chemical composition of tobacco and tobacco smoke." Chemical Reviews 68.2 (1968): 153-207. (Year: 1968).*
NCBI GenBank database entry document for EST CK294680, retrieved from www.ncbi.nlm.nih.gov/nucest/CK294680.1?report=genbank (Year: 2004).*
PCT International Search Report and Written Opinion dated Jan. 3, 2013 for PCT/EP2012/003663.
Database EMBL [Online] Apr. 15, 2006, "KF8C.108L21F.051215T7 KFB Nicotiana Tabacum cDNA Clone KF8C.108L21, mRNA Sequence." XP002668426, retrieved from EBI Accession No. EM_EST:EB426999 Database Accession No. EB426999 Sequence.
Bartlem et al., Mutation in the Threonine Synthase Gene Results in an Over-Accumulation of Soluble Methionine in Arabidopsis[1], *Plant Physiol.*, vol. 123, 2000, p. 101-110.

(Continued)

*Primary Examiner* — Weihua Fan
(74) *Attorney, Agent, or Firm* — Mueting, Raasch & Gebhardt, P.A.

(57) ABSTRACT

There is disclosed a mutant, non-naturally occurring or transgenic plant cell comprising: (i) a polynucleotide comprising, consisting or consisting essentially of a sequence encoding a threonine synthase and having at least 90% sequence identity to SEQ ID NO:1, SEQ ID NO:2 or SEQ ID NO:3 or at least 87% sequence identity to SEQ ID NO:4, or SEQ ID NO:5; (ii) a polypeptide encoded by any one of said polynucleotides set forth in (i); or (iii) a polypeptide having at least 95% sequence identity to SEQ ID NO:6, SEQ ID NO:7 or SEQ ID NO:8; or (iv) a construct, vector or expression vector comprising the polynucleotide as set forth in (i).

16 Claims, 1 Drawing Sheet
Specification includes a Sequence Listing.

(56) References Cited

OTHER PUBLICATIONS

PCT International Preliminary Examination Report dated Mar. 4, 2014 for PCT/EP2012/003663 (7 pages).
EP Search Report for European Application No. 11 17 9889 dated Jan. 31, 2012 (6 pages).
Azevedo et al., "The Aspartic Acid Metabolic Pathway, An Exciting and Essential Pathway in Plants," *Amino Acids*, 30:143-62.
Di et al., "Enhancement of the Primary Flavour Compound Methional in Potato by Increasing the Level of Soluble Methionine,"*J Agric Food Chem*, 51:5695:702.
Mandin et al., "Volatile Compounds From Potato-Like Model Systems,", *J Agric Food Chem*, 47:2355-9.
Zeh et al., "Antisense Inhibition of Threonine Synthase Leads to High Methionine Content in Transgenic Potato Plants," *Plant Physiol.*, 127:792-802.
Office Action issued in Singapore for Application No. 11201400216V dated Nov. 14, 2014 (7 pages).
Office Action issued in China for Application No. 2015022800637980 dated Mar. 4, 2015 (12 pages). English translation included.
Australian Examination Report for Application No. 2012301350 dated Apr. 1, 2015 (7 pages).
Office Action issued in Japan for Application No. 2014-527531 dated May 16, 2016 (11 pages).
Office Action issued in Australia for Application No. 2012301350 dated Feb. 5, 2016 (3 pages).
Office Action issued in Israel for Application No. 231100 dated Feb. 24, 2016 (2 pages). English translation included.
Office Action issued in China for Application No. 201280053702.5 dated Aug. 15, 2016 (4 pages). English translation only.
Office Action issued in Israeli for Application No. 231100 dated Jul. 7, 2016 (2 pages). English translation only.
Examination Report issued in Europe for Application No. 12758405.0 dated Sep. 29, 2016 (5 pages).
Examination Report issued in Singapore for Application No. 11201400216V dated Jul. 15, 2016 (7 pages).
Breitender et al., "Rapid Production of Recombinant Allergens in Nicotiana Benthamiana and Their Impact on Diagnosis and Therapy," *Int. Arch. Allergy Immunol.*, Jan. 24, 2012, vol. 124, No. 1-3, pp. 48-50.
Hacham et al., "Lysine Enhances Methionine Content by Modulating the Expression of S-adenosylmethionine Synthase,", *Plant. J.*, Jul. 7, 2007, vol. 51, No. 5, pp. 850-861.
Lindbo, "High-Efficiency Protein Expression in Plants from Agroinfection-Compatible Tobacco Mosaic Virus Expression Vectors," *BMC Biotechnol.*, Aug. 27, 2007, vol. 7:52.
Sparkes et al., "Rapid, Transient Expression of Fluorescent Fusion Proteins in Tobacco Plants and Generation of Stably Transformed Plants," *Nat. Protocols.*, Nov. 30, 2006, vol. 1, pp. 2019-2025.
Thomas et al., "Production of Therapeutic Proteins in Plants," *Agricultural Biotechnology in California Series*, 2002, pp. 1-12.
Examination Report issued in Japan for Application No. 2014-527531 dated Mar. 10, 2017 (10 pages). English translation included.
Examination Report issued in China for Application No. 201280053702.5 dated Mar. 17, 2017 (10 pages). English translation included.
Xiao Xiexhong, et al., "Tobacco Chemistry" China Agriculture Science and Technology Press, Apr. 1997, pp. 100-110.
Examination Report issued in Russia for Application No. 2014112759/10 dated Feb. 2, 2017 (15 pages). English translation included.
Frankel et al., "Characterization of Diphtheria Fusion Proteins Targeted to the Human Interleukin-3 Receptor", *Protein Engineering*, vol. 13, No. 8, pp. 575-581, 2000.
Office Action issued in Europe for Application No. 12758405.0-1401 dated Jun. 7, 2017 (5 pages).
Lucker et al., "Increased and Altered Fragrance of Tobacco Plants After Metabolic Engineering Using Three Monoterpene Synthases from Lemon", *Plant Physiology, American Society of Plant Physiologists*, Rockville, MD, vol. 134, No. 1, Jan. 1, 2004, pp. 510-519.
Office Action issued in Ukraine for Application No. a 2014 03275 (7 pages).
Office Action issued in Israeli for Application No. 231100 (6 pages).
Office Action issued in Mexico for Application No. MX/a/2014/002498 dated Dec. 18, 2017 (2 pages). English translation only.

\* cited by examiner

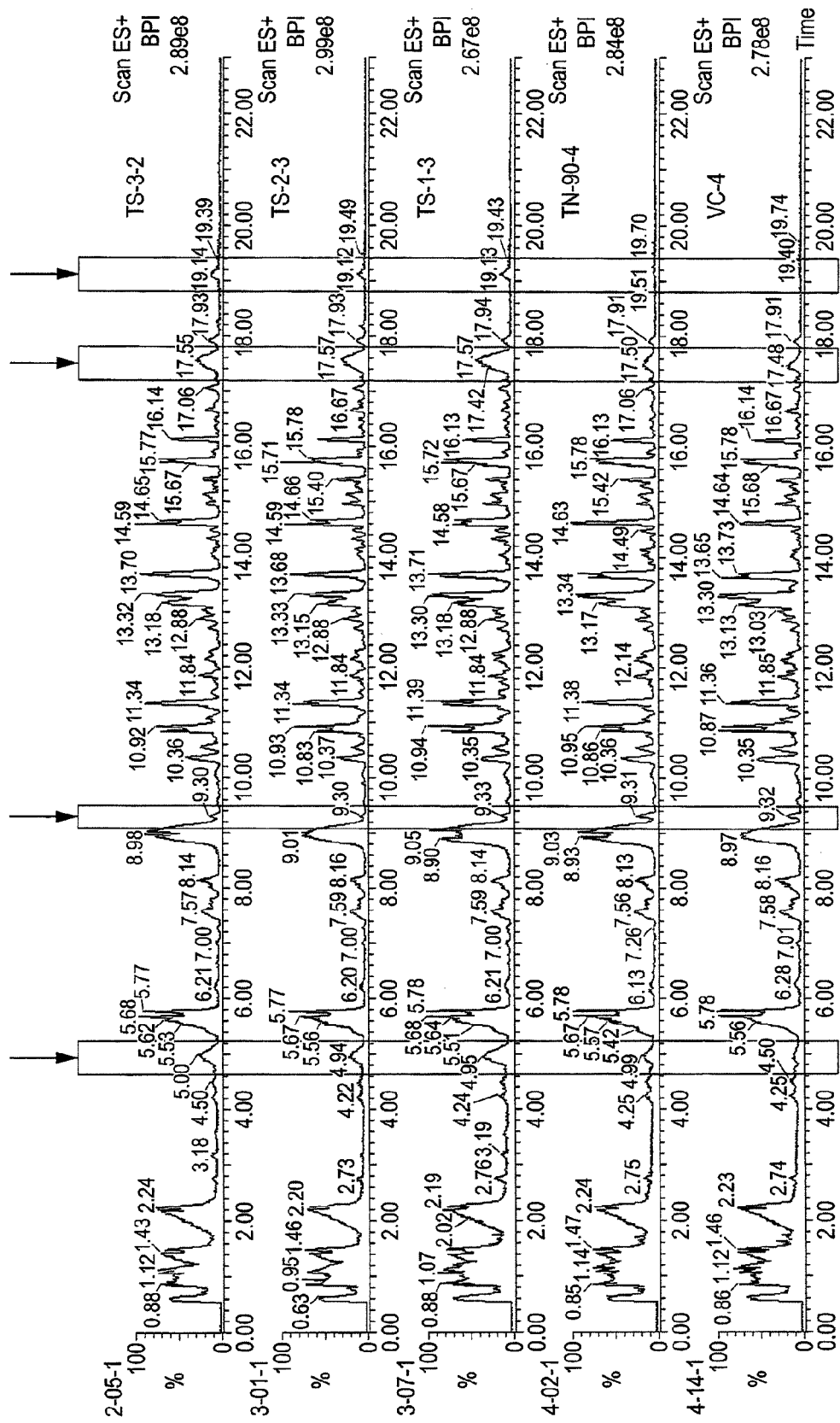

US 10,501,732 B2

SEQUENCE LISTING

<160> NUMBER OF SEQ ID NOS: 19

<210> SEQ ID NO 1
<211> LENGTH: 1569
<212> TYPE: DNA
<213> ORGANISM: Nicotiana tabacum

<400> SEQUENCE: 1
atggcggctt ctttcatgct cagatcttct ttcctctctc ctccttgttc ccaactccat     60
caccaatccc cttccaaatc taatcacatt attcacttca ttaatccaat caaagccacc    120
gcctctacaa atgacgcaat tgtccctccc aaaagcacc gccgcccgc cgacgaaaac    180 atccgcgaag aggcggcgcg ccgccgcacc tcctcccaca atttctccgc caggtacgtt    240
cctttcaatg ccgatcccag ctccgacgaa tggtattctc tcgatgaaat tataccgg    300

```
agccgctccg gtggattact tgatgttcag catgatatgg acgctctgaa gaaatttgat      360
ggccagtatt ggcggtcact gtttgattca cgtgtcggta agaccacgtg gccgtacggt      420
tcaggcgttt ggtctaaaaa ggaatgggtc ctacctgaaa tcgacagcga tgatattgtt      480
agtgcttttg aaggaaactc taatctgttt tgggctgagc gttttggcaa acagtttcta      540
ggcatgagtg acttatgggt aaaacactgt ggaatcagcc atacgggtag ttttaaggat      600
ctgggtatga ccgttttggt gagtcaagtg aaccggttaa ggaaaatgca taaaccagtt      660
gtaggtgtgg gctgtgcttc cactggtgac acgtcagctg cattgtcagc ttactgtgca      720
tctgcgggga ttccatccat tgtattttta ccagcaaata agatatctat ggcgcagctg      780
gtacaaccaa tagctaacgg agcttttgtg ttgagtattg acaccgattt tgatggttgt      840
atgcagttga ttcgcgaagt cactgcagag ttgcctattt acttggcgaa ttcgttgaat      900
agtttgaggt tagaagggca aaagactgca gcaattgaga ttttgcagca gtttgatggc      960
aaagtacccg attgggtgat agtacctgga gggaacttgg gtaatatata tgctttctat     1020
aaaggtttta tgatgtgcag agagttgggg ctagttgacc gtatccctag gcttgtgtgt     1080
gctcaagcag ctaacgctaa tccgctttac ttgcattata aatccggttg gaaagacttt     1140
caacccgtga aggcgaacac cacatttgca tctgctatac agattggtga tccagtgtct     1200
atagatagag ctgttttttgc cctgaagaac tgtgacggga tagttgagga ggcaacggag     1260
gaggagttga tggatgctat ggctcaggca gactcaactg ggatgttcat ttgcccgcac     1320
actggtgtgg cattgactgc cctgttcaag ttgagaaaca gtggagttat tggaccaaat     1380
gataagactg tggttgtgag tacagcacat ggattgaagt ttactcaatc aaagattgat     1440
taccactcaa aggaaataaa ggacatggaa tgtcggtttg ctaacccacc tgtggaagtg     1500
aaagcagatt ttggatcagt catggatgtt ctcaagaaat atttgttgag caaaaatgcc     1560
aagcactga                                                             1569
```

<210> SEQ ID NO 2
<211> LENGTH: 1569
<212> TYPE: DNA
<213> ORGANISM: Nicotiana tabacum

<400> SEQUENCE: 2

```
atggcggctt ctttcatgct cagatcttct ttcctctctc ctccttctcc ccaactccat       60
caccaatccc cttccaaatc taatcacact attcacttca tcaatccaat caaagccacc      120
gcctctacaa atgacgcaat tatccctccc cagaaacatc gtcgccccgc cgacgaaaac      180
atccgcgaag aggcggcgcg ccggcccacc tcctcccaca atttctccgc caggtacgtt      240
cctttcaatg ccgaccccag ctccgacgaa tggtattctc tcgatgaaat tatataccgg      300
agccgctccg gtggcttact tgatgttcag catgatatgg acgctctgaa gaaatttgat      360
ggccagtatt ggcggtcact gtttgattca cgtgtcggta agaccacgtg gccgtacggt      420
tcaggcgttt ggtctaaaaa ggaatgggtc ctacctgaaa tcgatagtga tgatattgtt      480
agtgcttttg aaggaaactc taatctgttt tgggctgagc gttttggtaa acagtttcta      540
ggcatgagtg acttatgggt aaaacactgt ggaattagcc atacaggtag ttttaaggat      600
ctgggtatga ccgttttggt gagtcaagtg aaccggttaa ggaaaatgca taaaccggtt      660
gttggtgtgg gctgtgcttc cactggtgac acgtcagctg cattgtcagc ttactgtgca      720
tctgcgggga ttccatcgat tgtattttta cctgcaaata agatatctat ggcgcagctg      780
```

| | |
|---|---|
| gtacaaccga tagctaacgg agcttttgtg ttgagcattg acaccgattt tgatggttgt | 840 |
| atgcagttga ttcgtgaagt cactgctgag ttgccaattt acttggcgaa ttctttgaat | 900 |
| agtttgaggt tagaagggca aaagactgca gcaattgaga ttttgcagca gtttgattgg | 960 |
| caagttcccg attgggtgat agttcctgga ggtaacttgg gtaatatata tgcgttctat | 1020 |
| aaaggtttta tgatgtgcaa agagttgggg ctcgttgatc gtatccctag gcttgtgtgt | 1080 |
| gctcaagcag ctaacgctaa tccgctttac ttgcattata aatccggttg gaaagacttt | 1140 |
| caacccgtga aggcgaacac cacatttgca tctgctatac agattggtga cccagtgtct | 1200 |
| atagatagag ctgttttttgc cctgaagaac tgtgacggga tagtggagga ggcaacggag | 1260 |
| gaggagttga tggatgctat ggctcaggca gactcaactg ggatgttcat ttgcccgcac | 1320 |
| actggtgtgg cattgactgc cctgttcaag ttgagaaaca gtggagttat cgggccaaat | 1380 |
| gataagactg tggttgtgag tacagcacat ggattgaagt ttactcaatc aaagattgat | 1440 |
| taccactcaa aggaaataaa ggacatggaa tgtcggtttg ctaacccacc tgtggaagtg | 1500 |
| aaagcagatt ttggatcagt catggatgtt ctcaagaaat atttgttgag caaaaatgcc | 1560 |
| aagcactga | 1569 |

<210> SEQ ID NO 3
<211> LENGTH: 1569
<212> TYPE: DNA
<213> ORGANISM: Nicotiana tabacum

<400> SEQUENCE: 3

| | |
|---|---|
| atggcggctt ctttcatgct cagatcttct ttcctctctc ctccttctcc ccaactccat | 60 |
| caccaatctc ctcctaaatc caatcccact attcacttca tcaatccaat caaagccacc | 120 |
| gcctctacaa atgacgcaat tatccctccc cagaaacacc gccgccctgc cgacgaaaat | 180 |
| atccgcgaag aggccgctcg ccgccccacc tcctcccaca atttctccgc caggtacgtg | 240 |
| cctttcaatg cggatccaag ctccgatgaa tggtattctc tcgatgaaat catctaccgg | 300 |
| agccgctccg gcggcctact tgatgttcaa catgatatgg acgctttaaa aaagtttgac | 360 |
| ggtcagtact ggaggtcact ttttgattca cgtgtcggga agacgacgtg gccttacggg | 420 |
| tcaggtgttt ggtctaagaa ggaatgggtc ctacccgaaa tcgatagtga tgatattgtt | 480 |
| agtgcttttg aaggaaactc aaatcttttt tgggctgagc gttttggcaa acagtttcta | 540 |
| ggcatgagtg atttatgggt aaaacactgt ggaattagtc atacaggtag tttttaaggat | 600 |
| ctaggtatga ctgttttggt gagtcaagtg aaccggttaa ggaaaatgca taaaccggtt | 660 |
| gttggtgtgg gctgtgcttc cactggtgac acgtcagctg cattgtcagc ttactgtgca | 720 |
| tctgcgggga ttccatcgat tgtatttta cctgcaaata agatatctat ggcgcagctg | 780 |
| gtacaaccga tagctaacgg agcttttgtg ttgagcattg acaccgattt tgatggttgt | 840 |
| atgcagttga ttcgtgaagt cactgctgag ttgccaattt acttggcgaa ttcgttgaat | 900 |
| agtttgaggt tagaagggca aaagactgca gcaattgaga ttttgcagca gtttgattgg | 960 |
| caagttcccg attgggtgat agttcctgga gggaacttgg gtaatatata tgcgttctat | 1020 |
| aaaggtttta tgatgtgcaa agagttgggg ctcgttgatc gtatccctag gcttgtgtgt | 1080 |
| gctcaagcag ctaacgcgaa tccgctttat ttgcattata aatccggttg gaaagacttt | 1140 |
| caacccgtga aggcgaacac cacatttgca tctgctatac agattggtga cccagtgtct | 1200 |
| atagatagag ctgttttttgc cctgaagaac tgtgacggga tagtggagga ggcaacagag | 1260 |
| gaggagttga tggatgctat ggctaaggca gactcgactg ggatgttcat ttgcccgcac | 1320 |

| | |
|---|---|
| actggtgtgg cattgactgc cctgttcaag ttgagaaaca gtggagttat cggaccaaat | 1380 |
| gataagaccg tggttgtgag tacagcacat ggattgaagt ttactcaatc aaagattgat | 1440 |
| tatcactcaa aggaaataaa ggacatggaa tgtcggtttg ctaacccacc tgtggaagtg | 1500 |
| aaagcagatt ttggatcagt catggatgtt ctcaagaaat atttgttgag caaaaatgcc | 1560 |
| aagcactga | 1569 |

<210> SEQ ID NO 4
<211> LENGTH: 1740
<212> TYPE: DNA
<213> ORGANISM: Nicotiana tabacum

<400> SEQUENCE: 4

| | |
|---|---|
| cgcagctgct ttaactattt tcgacactcc attaatggcg gcttctttca tgctcagatc | 60 |
| ttctttcctc tctcctcctt ctccccaact ccatcaccaa tctcctccta aatccaatcc | 120 |
| cactattcac ttcatcaatc caatcaaagc caccgcctct acaaatgacg caattatccc | 180 |
| tccccagaaa caccgccgcc ctgccgacga aaatatccgc gaagaggccg ctcgccgccc | 240 |
| cacctcctcc cacaatttct ccgccaggta tgtaggggaa gatatactag cgaaatgaat | 300 |
| agataataag caaaatgaaa atagtgggtc taaaattaca ataatttact cattgctcat | 360 |
| ttatttaatg ctgacatcaa aaagtgctgc gtatgtcact gcaggtacgt gcctttcaat | 420 |
| gcggatccaa gctccgatga atggtattct ctcgatgaaa tcatctaccg gagccgctcc | 480 |
| ggcggcctac ttgatgttca acatgatatg gacgctttaa aaaagtttga cggtcagtac | 540 |
| tggaggtcac tttttgattc acgtgtcggg aagacgacgt ggccttacgg gtcaggtgtt | 600 |
| tggtctaaga aggaatgggt cctacccgaa atcgatagtg atgatattgt tagtgctttt | 660 |
| gaaggaaact caaatctttt ttgggctgag cgttttggca aacagtttct aggcatgagt | 720 |
| gatttatggg taaaacactg tggaattagt catacaggta gttttaagga tctaggtatg | 780 |
| actgttttgg tgagtcaagt gaaccggtta aggaaaatgc ataaaccggt tgttggtgtg | 840 |
| ggctgtgctt ccactggtga cacgtcagct gcattgtcag cttactgtgc atctgcgggg | 900 |
| attccatcga ttgtattttt acctgcaaat aagatatcta tggcgcagct ggtacaaccg | 960 |
| atagctaacg gagcttttgt gttgagcatt gacaccgatt ttgatggttg tatgcagttg | 1020 |
| attcgtgaag tcactgctga gttgccaatt tacttggcga attcgttgaa tagttttgagg | 1080 |
| ttagaagggc aaaagactgc agcaattgag attttgcagc agtttgattg gcaagttccc | 1140 |
| gattgggtga tagttcctgg agggaacttg gtaatatat atgcgttcta taaaggttt | 1200 |
| atgatgtgca aagagttggg gctcgttgat cgtatcccta ggcttgtgtg tgctcaagca | 1260 |
| gctaacgcga atccgcttta tttgcattat aaatccggtt ggaaagactt caacccgtg | 1320 |
| aaggcgaaca ccacatttgc atctgctata cagattggtg acccagtgtc tatagataga | 1380 |
| gctgtttttg ccctgaagaa ctgtgacggg atagtgagg aggcaacaga ggaggagttg | 1440 |
| atggatgcta tggctaaggc agactcgact gggatgttca tttgcccgca cactggtgtg | 1500 |
| gcattgactg ccctgttcaa gttgagaaac agtggagtta tcggaccaaa tgataagacc | 1560 |
| gtggttgtga gtacagcaca tggattgaag tttactcaat caaagattga ttatcactca | 1620 |
| aaggaaataa aggacatgga atgtcggttt gctaacccac ctgtggaagt gaaagcagat | 1680 |
| tttggatcag tcatggatgt tctcaagaaa tatttgttga gcaaaaatgc caagcactga | 1740 |

<210> SEQ ID NO 5

<211> LENGTH: 1740
<212> TYPE: DNA
<213> ORGANISM: Nicotiana tomentosiformis

<400> SEQUENCE: 5

```
cgcagctgct ttaactattt tcgacactcc attaatggcg gcttctttca tgctcagata      60
ttctttcctc tctcctcctt ctccccaact ccatcaccaa tctcctccta aatccaatcc     120
cactattcac ttcatcaatc caatcaaagc caccgcctct acaaatgacg caattatccc     180
tccccagaaa caccgccgcc ctgccgacga aaatatccgc gaagaggccg ctcgccgccc     240
cacctcctcc cacaatttct ccgccaggta tgtaggggaa gatatactag cgaaatgaat     300
agataataag caaaatgaaa atagtgggtc taaaattaca ataatttact cattgctcat     360
ttatttaatg ctgacatcaa aaagtgctgc gtatgtcact gcaggtacgt gcctttcaat     420
gcggatccaa gctccgatga atggtattct ctcgatgaaa tcatctaccg gagccgctcc     480
ggcggcctac ttgatgttca acatgatatg gacgctttaa aaaagtttga cggtcagtac     540
tggaggtcac ttttttgattc acgtgtcggg aagacgacgt ggccttacgg gtcaggtgtt     600
tggtctaaga aggaatgggt cctacccgaa atcgatagtg atgatattgt tagtgctttt     660
gaaggaaaact caaatctttt ttgggctgag cgttttggca acagtttctt aggcatgagt     720
gatttatggg taaaacactg tggaattagt catacaggta gttttaagga tctaggtatg     780
actgttttgg tgagtcaagt gaaccggtta aggaaaatgc ataaaccggt tgttggtgtg     840
ggctgtgctt ccactggtga cacgtcagct gcattgtcag cttactgtgc atctgcgggg     900
attccatcga ttgtatttt acctgcaaat aagtatctca tggcgcagct ggtacaaccg     960
atagctaacg gagcttttgt gttgagcatt gacaccgatt ttgatggttg tatgcagttg    1020
attcgtgaag tcactgctga gttgccaatt tacttggcga attcgttgaa tagttttgagg    1080
ttagaagggc aaaagactgc agcaattgag atttttgcagc agtttgattg gcaagttccc    1140
gattgggtga tagttcctgg agggaacttg ggtaatatat atgcgttcta taaaggtttt    1200
atgatgtgca aagagttggg gctcgttgat cgtatcccta ggcttgtgtg tgctcaagca    1260
gctaacgcga atccgcttta tttgcattat aaatccggtt ggaaagactt tcaacccgtg    1320
aaggcgaaca ccacatttgc atctgctata cagattggtg acccagtgtc tatagataga    1380
gctgtttttg ccctgaagaa ctgtgacggg atagtggagg aggcaacaga ggaggagttg    1440
atggatgcta tggctcaggc agactcgact gggatgttca tttgcccgca cactggtgtg    1500
gcattgactg ccctgttcaa gtcgagaaac agtggagtta tcggaccaaa tgataagacc    1560
gtggttgtga gtacagcaca tggattgaag tttactcaat caaagattga ttatcactca    1620
aaggaaataa aggacatgga atgtcggttt gctaacccac ctgtggaagt gaaagcagat    1680
tttggatcag tcatggatgt tctcaagaaa tatttgttga gcaaaaatgc caagcactga    1740
```

<210> SEQ ID NO 6
<211> LENGTH: 522
<212> TYPE: PRT
<213> ORGANISM: Nicotiana tabacum

<400> SEQUENCE: 6

Met Ala Ala Ser Phe Met Leu Arg Ser Ser Phe Leu Ser Pro Pro Cys
1               5                   10                  15

Ser Gln Leu His His Gln Ser Pro Ser Lys Ser Asn His Ile Ile His
            20                  25                  30

Phe Ile Asn Pro Ile Lys Ala Thr Ala Ser Thr Asn Asp Ala Ile Val

```
                35                  40                  45
Pro Pro Gln Lys His Arg Arg Pro Ala Asp Glu Asn Ile Arg Glu Glu
 50                  55                  60

Ala Ala Arg Arg Thr Ser Ser His Asn Phe Ser Ala Arg Tyr Val
 65                  70                  75                  80

Pro Phe Asn Ala Asp Pro Ser Ser Asp Glu Trp Tyr Ser Leu Asp Glu
                     85                  90                  95

Ile Ile Tyr Arg Ser Arg Ser Gly Gly Leu Leu Asp Val Gln His Asp
                100                 105                 110

Met Asp Ala Leu Lys Lys Phe Asp Gly Gln Tyr Trp Arg Ser Leu Phe
                115                 120                 125

Asp Ser Arg Val Gly Lys Thr Thr Trp Pro Tyr Gly Ser Gly Val Trp
130                 135                 140

Ser Lys Lys Glu Trp Val Leu Pro Glu Ile Asp Ser Asp Ile Val
145                 150                 155                 160

Ser Ala Phe Glu Gly Asn Ser Asn Leu Phe Trp Ala Glu Arg Phe Gly
                165                 170                 175

Lys Gln Phe Leu Gly Met Ser Asp Leu Trp Val Lys His Cys Gly Ile
                180                 185                 190

Ser His Thr Gly Ser Phe Lys Asp Leu Gly Met Thr Val Leu Val Ser
                195                 200                 205

Gln Val Asn Arg Leu Arg Lys Met His Lys Pro Val Val Gly Val Gly
210                 215                 220

Cys Ala Ser Thr Gly Asp Thr Ser Ala Ala Leu Ser Ala Tyr Cys Ala
225                 230                 235                 240

Ser Ala Gly Ile Pro Ser Ile Val Phe Leu Pro Ala Asn Lys Ile Ser
                245                 250                 255

Met Ala Gln Leu Val Gln Pro Ile Ala Asn Gly Ala Phe Val Leu Ser
                260                 265                 270

Ile Asp Thr Asp Phe Asp Gly Cys Met Gln Leu Ile Arg Glu Val Thr
                275                 280                 285

Ala Glu Leu Pro Ile Tyr Leu Ala Asn Ser Leu Asn Ser Leu Arg Leu
290                 295                 300

Glu Gly Gln Lys Thr Ala Ala Ile Glu Ile Leu Gln Gln Phe Asp Gly
305                 310                 315                 320

Lys Val Pro Asp Trp Val Ile Val Pro Gly Gly Asn Leu Gly Asn Ile
                325                 330                 335

Tyr Ala Phe Tyr Lys Gly Phe Met Met Cys Arg Glu Leu Gly Leu Val
                340                 345                 350

Asp Arg Ile Pro Arg Leu Val Cys Ala Gln Ala Ala Asn Ala Asn Pro
                355                 360                 365

Leu Tyr Leu His Tyr Lys Ser Gly Trp Lys Asp Phe Gln Pro Val Lys
                370                 375                 380

Ala Asn Thr Thr Phe Ala Ser Ala Ile Gln Ile Gly Asp Pro Val Ser
385                 390                 395                 400

Ile Asp Arg Ala Val Phe Ala Leu Lys Asn Cys Asp Gly Ile Val Glu
                405                 410                 415

Glu Ala Thr Glu Glu Leu Met Asp Ala Met Ala Gln Ala Asp Ser
                420                 425                 430

Thr Gly Met Phe Ile Cys Pro His Thr Gly Val Ala Leu Thr Ala Leu
                435                 440                 445

Phe Lys Leu Arg Asn Ser Gly Val Ile Gly Pro Asn Asp Lys Thr Val
450                 455                 460
```

```
Val Val Ser Thr Ala His Gly Leu Lys Phe Thr Gln Ser Lys Ile Asp
465                 470                 475                 480

Tyr His Ser Lys Glu Ile Lys Asp Met Glu Cys Arg Phe Ala Asn Pro
            485                 490                 495

Pro Val Glu Val Lys Ala Asp Phe Gly Ser Val Met Asp Val Leu Lys
        500                 505                 510

Lys Tyr Leu Leu Ser Lys Asn Ala Lys His
        515                 520

<210> SEQ ID NO 7
<211> LENGTH: 522
<212> TYPE: PRT
<213> ORGANISM: Nicotiana tabacum

<400> SEQUENCE: 7

Met Ala Ala Ser Phe Met Leu Arg Ser Ser Phe Leu Ser Pro Pro Ser
1               5                   10                  15

Pro Gln Leu His His Gln Ser Pro Ser Lys Ser Asn His Thr Ile His
            20                  25                  30

Phe Ile Asn Pro Ile Lys Ala Thr Ala Ser Thr Asn Asp Ala Ile Ile
            35                  40                  45

Pro Pro Gln Lys His Arg Arg Pro Ala Asp Glu Asn Ile Arg Glu Glu
    50                  55                  60

Ala Ala Arg Arg Pro Thr Ser Ser His Asn Phe Ser Ala Arg Tyr Val
65                  70                  75                  80

Pro Phe Asn Ala Asp Pro Ser Ser Asp Glu Trp Tyr Ser Leu Asp Glu
            85                  90                  95

Ile Ile Tyr Arg Ser Arg Ser Gly Gly Leu Leu Asp Val Gln His Asp
            100                 105                 110

Met Asp Ala Leu Lys Lys Phe Asp Gly Gln Tyr Trp Arg Ser Leu Phe
            115                 120                 125

Asp Ser Arg Val Gly Lys Thr Thr Trp Pro Tyr Gly Ser Gly Val Trp
    130                 135                 140

Ser Lys Lys Glu Trp Val Leu Pro Glu Ile Asp Ser Asp Asp Ile Val
145                 150                 155                 160

Ser Ala Phe Glu Gly Asn Ser Asn Leu Phe Trp Ala Glu Arg Phe Gly
            165                 170                 175

Lys Gln Phe Leu Gly Met Ser Asp Leu Trp Val Lys His Cys Gly Ile
            180                 185                 190

Ser His Thr Gly Ser Phe Lys Asp Leu Gly Met Thr Val Leu Val Ser
            195                 200                 205

Gln Val Asn Arg Leu Arg Lys Met His Lys Pro Val Val Gly Val Gly
    210                 215                 220

Cys Ala Ser Thr Gly Asp Thr Ser Ala Ala Leu Ser Ala Tyr Cys Ala
225                 230                 235                 240

Ser Ala Gly Ile Pro Ser Ile Val Phe Leu Pro Ala Asn Lys Ile Ser
            245                 250                 255

Met Ala Gln Leu Val Gln Pro Ile Ala Asn Gly Ala Phe Val Leu Ser
            260                 265                 270

Ile Asp Thr Asp Phe Asp Gly Cys Met Gln Leu Ile Arg Glu Val Thr
            275                 280                 285

Ala Glu Leu Pro Ile Tyr Leu Ala Asn Ser Leu Asn Ser Leu Arg Leu
    290                 295                 300

Glu Gly Gln Lys Thr Ala Ala Ile Glu Ile Leu Gln Gln Phe Asp Trp
```

```
            305                 310                 315                 320
    Gln Val Pro Asp Trp Val Ile Val Pro Gly Gly Asn Leu Gly Asn Ile
                    325                 330                 335

Tyr Ala Phe Tyr Lys Gly Phe Met Met Cys Lys Glu Leu Gly Leu Val
                    340                 345                 350

Asp Arg Ile Pro Arg Leu Val Cys Ala Gln Ala Ala Asn Ala Asn Pro
                    355                 360                 365

Leu Tyr Leu His Tyr Lys Ser Gly Trp Lys Asp Phe Gln Pro Val Lys
                    370                 375                 380

Ala Asn Thr Thr Phe Ala Ser Ala Ile Gln Ile Gly Asp Pro Val Ser
    385                 390                 395                 400

Ile Asp Arg Ala Val Phe Ala Leu Lys Asn Cys Asp Gly Ile Val Glu
                    405                 410                 415

Glu Ala Thr Glu Glu Leu Met Asp Ala Met Ala Gln Ala Asp Ser
                    420                 425                 430

Thr Gly Met Phe Ile Cys Pro His Thr Gly Val Ala Leu Thr Ala Leu
                    435                 440                 445

Phe Lys Leu Arg Asn Ser Gly Val Ile Gly Pro Asn Asp Lys Thr Val
                    450                 455                 460

Val Val Ser Thr Ala His Gly Leu Lys Phe Thr Gln Ser Lys Ile Asp
    465                 470                 475                 480

Tyr His Ser Lys Glu Ile Lys Asp Met Glu Cys Arg Phe Ala Asn Pro
                    485                 490                 495

Pro Val Glu Val Lys Ala Asp Phe Gly Ser Val Met Asp Val Leu Lys
                    500                 505                 510

Lys Tyr Leu Leu Ser Lys Asn Ala Lys His
                    515                 520

<210> SEQ ID NO 8
<211> LENGTH: 522
<212> TYPE: PRT
<213> ORGANISM: Nicotiana tabacum

<400> SEQUENCE: 8

Met Ala Ala Ser Phe Met Leu Arg Ser Ser Phe Leu Ser Pro Pro Ser
    1               5                   10                  15

Pro Gln Leu His His Gln Ser Pro Pro Lys Ser Asn Pro Thr Ile His
                    20                  25                  30

Phe Ile Asn Pro Ile Lys Ala Thr Ala Ser Thr Asn Asp Ala Ile Ile
                    35                  40                  45

Pro Pro Gln Lys His Arg Arg Pro Ala Asp Glu Asn Ile Arg Glu Glu
                    50                  55                  60

Ala Ala Arg Arg Pro Thr Ser Ser His Asn Phe Ser Ala Arg Tyr Val
    65                  70                  75                  80

Pro Phe Asn Ala Asp Pro Ser Ser Asp Glu Trp Tyr Ser Leu Asp Glu
                    85                  90                  95

Ile Ile Tyr Arg Ser Arg Ser Gly Gly Leu Leu Asp Val Gln His Asp
                    100                 105                 110

Met Asp Ala Leu Lys Lys Phe Asp Gly Gln Tyr Trp Arg Ser Leu Phe
                    115                 120                 125

Asp Ser Arg Val Gly Lys Thr Thr Trp Pro Tyr Gly Ser Gly Val Trp
                    130                 135                 140

Ser Lys Lys Glu Trp Val Leu Pro Glu Ile Asp Ser Asp Asp Ile Val
    145                 150                 155                 160
```

```
Ser Ala Phe Glu Gly Asn Ser Asn Leu Phe Trp Ala Glu Arg Phe Gly
                165                 170                 175
Lys Gln Phe Leu Gly Met Ser Asp Leu Trp Val Lys His Cys Gly Ile
            180                 185                 190
Ser His Thr Gly Ser Phe Lys Asp Leu Gly Met Thr Val Leu Val Ser
        195                 200                 205
Gln Val Asn Arg Leu Arg Lys Met His Lys Pro Val Val Gly Val Gly
    210                 215                 220
Cys Ala Ser Thr Gly Asp Thr Ser Ala Ala Leu Ser Ala Tyr Cys Ala
225                 230                 235                 240
Ser Ala Gly Ile Pro Ser Ile Val Phe Leu Pro Ala Asn Lys Ile Ser
                245                 250                 255
Met Ala Gln Leu Val Gln Pro Ile Ala Asn Gly Ala Phe Val Leu Ser
            260                 265                 270
Ile Asp Thr Asp Phe Asp Gly Cys Met Gln Leu Ile Arg Glu Val Thr
        275                 280                 285
Ala Glu Leu Pro Ile Tyr Leu Ala Asn Ser Leu Asn Ser Leu Arg Leu
    290                 295                 300
Glu Gly Gln Lys Thr Ala Ala Ile Glu Ile Leu Gln Gln Phe Asp Trp
305                 310                 315                 320
Gln Val Pro Asp Trp Val Ile Val Pro Gly Gly Asn Leu Gly Asn Ile
                325                 330                 335
Tyr Ala Phe Tyr Lys Gly Phe Met Met Cys Lys Glu Leu Gly Leu Val
            340                 345                 350
Asp Arg Ile Pro Arg Leu Val Cys Ala Gln Ala Ala Asn Ala Asn Pro
        355                 360                 365
Leu Tyr Leu His Tyr Lys Ser Gly Trp Lys Asp Phe Gln Pro Val Lys
    370                 375                 380
Ala Asn Thr Thr Phe Ala Ser Ala Ile Gln Ile Gly Asp Pro Val Ser
385                 390                 395                 400
Ile Asp Arg Ala Val Phe Ala Leu Lys Asn Cys Asp Gly Ile Val Glu
                405                 410                 415
Glu Ala Thr Glu Glu Glu Leu Met Asp Ala Met Ala Lys Ala Asp Ser
            420                 425                 430
Thr Gly Met Phe Ile Cys Pro His Thr Gly Val Ala Leu Thr Ala Leu
        435                 440                 445
Phe Lys Leu Arg Asn Ser Gly Val Ile Gly Pro Asn Asp Lys Thr Val
    450                 455                 460
Val Val Ser Thr Ala His Gly Leu Lys Phe Thr Gln Ser Lys Ile Asp
465                 470                 475                 480
Tyr His Ser Lys Glu Ile Lys Asp Met Glu Cys Arg Phe Ala Asn Pro
                485                 490                 495
Pro Val Glu Val Lys Ala Asp Phe Gly Ser Val Met Asp Val Leu Lys
            500                 505                 510
Lys Tyr Leu Leu Ser Lys Asn Ala Lys His
        515                 520
```

<210> SEQ ID NO 9
<211> LENGTH: 21
<212> TYPE: DNA
<213> ORGANISM: Artificial sequence
<220> FEATURE:
<221> NAME/KEY: source
<222> LOCATION: 1..21
<223> OTHER INFORMATION: /note = "Description of artificial sequence: Primer"

<400> SEQUENCE: 9
ctgaaatcga cagcgatgat a                                              21

<210> SEQ ID NO 10
<211> LENGTH: 22
<212> TYPE: DNA
<213> ORGANISM: Artificial sequence
<220> FEATURE:
<221> NAME/KEY: source
<222> LOCATION: 1..22
<223> OTHER INFORMATION: /note = "Description of artificial sequence:
      Primer"

<400> SEQUENCE: 10
caaccaatag ctaacggagc tt                                             22

<210> SEQ ID NO 11
<211> LENGTH: 22
<212> TYPE: DNA
<213> ORGANISM: Artificial sequence
<220> FEATURE:
<221> NAME/KEY: source
<222> LOCATION: 1..22
<223> OTHER INFORMATION: /note = "Description of artificial sequence:
      Primer"

<400> SEQUENCE: 11
gagcatcgtg gaaaaagaag ac                                             22

<210> SEQ ID NO 12
<211> LENGTH: 22
<212> TYPE: DNA
<213> ORGANISM: Artificial sequence
<220> FEATURE:
<221> NAME/KEY: source
<222> LOCATION: 1..22
<223> OTHER INFORMATION: /note = "Description of artificial sequence:
      Primer"

<400> SEQUENCE: 12
aagctccgtt agctattggt tg                                             22

<210> SEQ ID NO 13
<211> LENGTH: 22
<212> TYPE: DNA
<213> ORGANISM: Artificial sequence
<220> FEATURE:
<221> NAME/KEY: source
<222> LOCATION: 1..22
<223> OTHER INFORMATION: /note = "Description of artificial sequence:
      Primer"

<400> SEQUENCE: 13
ttgattcacg tgtcggtaag ac                                             22

<210> SEQ ID NO 14
<211> LENGTH: 351
<212> TYPE: DNA
<213> ORGANISM: Artificial sequence
<220> FEATURE:
<221> NAME/KEY: source
<222> LOCATION: 1..351
<223> OTHER INFORMATION: /note = "Description of artificial sequence:
      RNAi sequence used to silence threonine synthase"

<400> SEQUENCE: 14
ctgaaatcga cagcgatgat attgttagtg cttttgaagg aaactctaat ctgttttggg    60

```
ctgagcgttt tggcaaacag tttctaggca tgagtgactt atgggtaaaa cactgtggaa      120
tcagccatac gggtagtttt aaggatctgg gtatgaccgt tttggtgagt caagtgaacc      180
ggttaaggaa aatgcataaa ccagttgtag gtgtgggctg tgcttccact ggtgacacgt      240
cagctgcatt gtcagcttac tgtgcatctg cggggattcc atccattgta ttttaccag       300 caaataagat atctatggcg cagctggtac aaccaatagc taacggagct t               351
```

<210> SEQ ID NO 15
<211> LENGTH: 351
<212> TYPE: DNA
<213> ORGANISM: Artificial sequence
<220> FEATURE:
<221> NAME/KEY: source
<222> LOCATION: 1..351
<223> OTHER INFORMATION: /note = "Description of artificial sequence:
      RNAi sequence used to silence threonine synthase"

<400> SEQUENCE: 15

```
ctgaaatcga tagtgatgat attgttagtg cttttgaagg aaactctaat ctgttttggg      60
ctgagcgttt tggtaaacag tttctaggca tgagtgactt atgggtaaaa cactgtggaa      120
ttagccatac aggtagtttt aaggatctgg gtatgaccgt tttggtgagt caagtgaacc      180
ggttaaggaa aatgcataaa ccggttgttg gtgtgggctg tgcttccact ggtgacacgt      240
cagctgcatt gtcagcttac tgtgcatctg cggggattcc atcgattgta ttttacctg      300 caaataagat atctatggcg cagctggtac aaccgatagc taacggagct t              351
```

<210> SEQ ID NO 16
<211> LENGTH: 351
<212> TYPE: DNA
<213> ORGANISM: Artificial sequence
<220> FEATURE:
<221> NAME/KEY: source
<222> LOCATION: 1..351
<223> OTHER INFORMATION: /note = "Description of artificial sequence:
      RNAi sequence used to silence threonine synthase"

<400> SEQUENCE: 16

```
ccgaaatcga tagtgatgat attgttagtg cttttgaagg aaactcaaat cttttttggg     60
ctgagcgttt tggcaaacag tttctaggca tgagtgattt atgggtaaaa cactgtggaa     120
ttagtcatac aggtagtttt aaggatctag gtatgactgt tttggtgagt caagtgaacc     180
ggttaaggaa aatgcataaa ccggttgttg gtgtgggctg tgcttccact ggtgacacgt     240
cagctgcatt gtcagcttac tgtgcatctg cggggattcc atcgattgta ttttacctg     300 caaataagat atctatggcg cagctggtac aaccgatagc taacggagct t             351
```

<210> SEQ ID NO 17
<211> LENGTH: 351
<212> TYPE: DNA
<213> ORGANISM: Artificial sequence
<220> FEATURE:
<221> NAME/KEY: source
<222> LOCATION: 1..351
<223> OTHER INFORMATION: /note = "Description of artificial sequence:
      RNAi sequence used to silence threonine synthase"

<400> SEQUENCE: 17

```
ccgaaatcga tagtgatgat attgttagtg cttttgaagg aaactcaaat cttttttggg     60
ctgagcgttt tggcaaacag tttctaggca tgagtgattt atgggtaaaa cactgtggaa     120
ttagtcatac aggtagtttt aaggatctag gtatgactgt tttggtgagt caagtgaacc     180
```

```
ggttaaggaa aatgcataaa ccggttgttg gtgtgggctg tgcttccact ggtgacacgt      240
cagctgcatt gtcagcttac tgtgcatctg cggggattcc atcgattgta tttttacctg      300
caaataagat atctatggcg cagctggtac aaccgatagc taacggagct t               351

<210> SEQ ID NO 18
<211> LENGTH: 351
<212> TYPE: DNA
<213> ORGANISM: Artificial sequence
<220> FEATURE:
<221> NAME/KEY: source
<222> LOCATION: 1..351
<223> OTHER INFORMATION: /note = "Description of artificial sequence:
      RNAi sequence used to silence threonine synthase"

<400> SEQUENCE: 18
ccgaaatcga tagtgatgat attgttagtg cttttgaagg aaactcaaat cttttttggg       60
ctgagcgttt tggcaaacag tttctaggca tgagtgattt atgggtaaaa cactgtggaa      120
ttagtcatac aggtagtttt aaggatctag gtatgactgt tttggtgagt caagtgaacc      180
ggttaaggaa aatgcataaa ccggttgttg gtgtgggctg tgcttccact ggtgacacgt      240
cagctgcatt gtcagcttac tgtgcatctg cggggattcc atcgattgta tttttacctg      300
caaataagat atctatggcg cagctggtac aaccgatagc taacggagct t               351

<210> SEQ ID NO 19
<211> LENGTH: 351
<212> TYPE: DNA
<213> ORGANISM: Artificial sequence
<220> FEATURE:
<221> NAME/KEY: source
<222> LOCATION: 1..351
<223> OTHER INFORMATION: /note = "Description of artificial sequence:
      RNAi sequence used to silence threonine synthase"

<400> SEQUENCE: 19
ctgaaatcga tagtgatgat attgttagtg cttttgaagg aaactctaat ctgttttggg       60
ctgagcgttt tggtaaacag tttctaggca tgagtgactt atgggtaaaa cactgtggaa      120
ttagccatac aggtagtttt aaggatctgg gtatgaccgt tttggtgagt caagtgaacc      180
ggttaaggaa aatgcataaa ccggttgttg gtgtgggctg tgcttccact ggtgacacgt      240
cagctgcatt gtcagcttac tgtgcatctg cggggattcc atcgattgta tttttacctg      300
caaataagat atctatggcg cagctggtac aaccgatagc taacggagct t               351
```

THREONINE SYNTHASE FROM NICOTIANA TABACUM AND METHODS AND USES THEREOF

This application is a National Stage Application of International Application No. PCT/EP2012/003663 filed Aug. 31, 2012, which was published in English on Mar. 7, 2013 as International Patent Publication WO 2013/029800 A1 and which claims priority to European Application No. 11179889.8, filed Sep. 2, 2011.

FIELD OF THE INVENTION

The present invention discloses the threonine synthase gene from *Nicotiana tabacum* and variants, homologues and fragments thereof. In particular, there is described the modification of the expression of this gene or the activity of the protein encoded thereby to increase the free methionine levels in plants—such as tobacco plants. This can be used to generate desirable tastes and aromas in tobacco by elevating levels of methional therein.

BACKGROUND OF THE INVENTION

An increase in flavours—such as aroma-producing substances—in tobacco can generate a desirable taste when the tobacco is smoked. Such flavours can be obtained, for example, from amino acids which are subjected to Maillard reactions. Methional (3-(methylthio)propanal) is a flavour compound responsible for a "baked potato" aroma. The production of methional can be induced thermally where methional originates from methionine and methionine derivatives. The Strecker degradation of methionine involves interaction with alpha-dicarbonyl compounds, which are intermediates in the Maillard reactions, and result in the formation of methional. Various methods for increasing the amount of free methionine in plants have been developed, for example, exogenous amino acids can be added to plants. However, the use of exogenously added amino acids results in a significant increase in production cost, as well as safety and regulatory concerns.

The biosynthesis of methionine and threonine are both linked to the aspartate pathway. In plants, their biosynthetic pathways diverge at the level of O-phosphohomoserine (OPH). The enzymes cystathionine gamma-synthase (CGS) and threonine synthase (TS) compete for the common substrate O-phosphohomoserine. Free methionine levels can potentially be increased by over-expressing or inhibiting expression of enzymes involved in the aspartate biosynthetic pathway.

One possible approach is to overexpress cystathionine gamma-synthase. Another approach is to decrease the expression of threonine synthase. However, to date all such efforts directed to alter threonine synthase genes resulted in phenotypes that adversely affected the entire plant. Bartlem et al. (2000) *Plant Physiol.*, 2000, 123:101-110) describes mutations in the threonine synthase gene of *Arabidopsis* plants. The disclosed mutants carrying a single base pair mutation within the gene encoding threonine synthase exhibited an over-accumulation of methionine and a markedly reduced level of threonine. However, the disclosed mutants of *Arabidopsis* suffered from reduced growth compared with that of the wild type. The stunted growth can be rescued only upon threonine or isoleucine addition.

Zeh et al. (2001) *Plant Physiol.*, 2001, 127:792-802 discloses transgenic potato plants prepared by an antisense transgenic approach using the constitutive cauliflower mosaic virus 35S promoter. Whilst the disclosed transgenic potato plants exhibited high levels of methionine, they also suffered from reduced growth as compared with that of the wild type plants.

Avraham et al. (2005) *Transgenic Research*, 2005, 14: 299-311 describes transgenic *Arabidopsis* plants that are prepared by an antisense transgenic approach. Whilst, the disclosed transgenic plants exhibited an increased level of methionine, they suffered from severely abnormal phenotypes, including considerable growth retardation, reduced rosette leaf size and chlorotic leaves.

There is a need for plants—such as tobacco plants—that combine an increased level of free methionine while maintaining certain agronomically desirable properties—such as growth rate and overall size of the plants—and without requiring the addition of any exogenous ingredients. It is an object of the present invention to satisfy this need.

ASPECTS AND EMBODIMENTS OF THE INVENTION

The present invention is based, at least in part, on the finding that a reduction (for example, inhibition) in threonine synthase expression or activity in plants or plant cells—such as tobacco plants or plant cells—results in an increase in methionine concentration, in plant cells or one or more parts of a plant as compared to a control plant or plant cell. Surprisingly, the genetically modified plant does not exhibit any change in its overall visual appearance as compared to a control plant. This finding is unexpected in view of the various adverse phenotypes observed in transgenic Arabidposis or potato plants. The finding can be advantageously exploited because plants are used for the commercial production of various products including tobacco where alterations in visual appearance would either not be acceptable to the industry or could result in unacceptably reduced production yields. The addition of exogenous amino acid is also not required. Moreover, the aerosol that is released upon heating the tobacco contains elevated level of methional as compared to tobacco prepared from a control plant. The increase in methional in the smoke or aerosol produces a desirable flavour, aroma, or both flavour and aroma when the tobacco is used.

Aspect and embodiments of the present invention are set forth in the accompanying claims.

In one aspect, there is provided an isolated polynucleotide comprising, consisting or consisting essentially of a sequence encoding a threonine synthase and having at least 90% sequence identity to SEQ ID NO:1, SEQ ID NO:2 or SEQ ID NO:3.

In another aspect, there is provided an isolated polynucleotide comprising, consisting or consisting essentially of a sequence encoding a threonine synthase and having at least 87% sequence identity to SEQ ID NO:4 or SEQ ID NO:5.

In a further aspect, there is provided an isolated polynucleotide comprising, consisting or consisting essentially of a sequence encoding a threonine synthase and having at least 70%, 75%, 80%, 85%, 90%, 95%, 96%, 97%, 98%, 99% or 100% sequence identity to SEQ ID NO:20.

In another aspect, there is provided an isolated polypeptide encoded by any one of the polynucleotides of the present invention.

In another aspect, there is provided an isolated polypeptide having at least 95% sequence identity to SEQ ID NO:6, SEQ ID NO:7 or SEQ ID NO:8.

In another aspect, there is provided an isolated polypeptide having at least 70%, 75%, 80%, 85%, 90%, 95%, 96%, 97%, 98%, 99% or 100% sequence identity to SEQ ID NO:21.

In another aspect, there is provided a construct, vector or expression vector comprising any one (for example, one or more, two or more, three or more or four or more) of the polynucleotides of the present invention.

In another aspect, there is provided a mutant, non-naturally occurring plant cell or a transgenic plant cell, comprising at least one (for example, one or more, two or more, three or more or four or more) of the polynucleotides, or at least one (for example, one or more, two or more, three or more or four or more) of the polypeptides. In another aspect, there is provided a mutant, non-naturally occurring plant or a transgenic plant comprising the plant cell according to the present invention. Suitably, expression of one or more threonine synthase coding sequences or the activity of the threonine synthase proteins encoded thereby is reduced, and a part of the tobacco plant has an increase in methionine content of at least 5% as compared to a control tobacco plant in which the expression or the activity of threonine synthase has not been reduced, or wherein the methional concentration in smoke or aerosol is increased by at least 5% as compared to the smoke or aerosol from the control tobacco plant.

A further aspect relates to a method for increasing the concentration of methionine in at least a part of a tobacco plant, comprising the steps of: (i) reducing the expression or activity of one or more threonine synthases (for example, two or more, three or more or four or more) in the tobacco plant, preferably, wherein the threonine synthase comprises the polynucleotide sequence or the polypeptide sequence described herein; (ii) measuring the concentration of methionine in at least a part of the mutant, non-naturally occurring or transgenic tobacco plant obtained in step (i); and (iii) identifying a mutant, non-naturally occurring plant or a transgenic tobacco plant in which the concentration of methionine therein has increased in comparison to a control plant. Preferably, the overall visual appearance of the mutant, non-naturally occurring plant or transgenic tobacco plant is substantially similar to the control tobacco plant, after a period such as three months after field transplant, or 36 days after topping.

In one embodiment, the addition of exogenous nutrients—such as amino acids—for example, threonine and/or isoleucine—is not required.

In another aspect, there is provided a mutant, non-naturally occurring tobacco plant or a transgenic tobacco plant, or tobacco plant material derived or derivable therefrom that is obtained or obtainable by said method.

In another aspect, there is also provided a mutant, non-naturally occurring tobacco plant or a transgenic tobacco plant, wherein expression of one or more threonine synthase coding sequences (for example, two or more, three or more or four or more) or the activity of the threonine synthase protein encoded thereby is reduced, and a part of the tobacco plant has an increase in methionine content of at least 5% as compared to a control tobacco plant in which the expression or the activity of threonine synthase has not been reduced, or wherein the methional concentration in smoke or aerosol is increased by at least 5% as compared to the to smoke or aerosol from the control tobacco plant.

Suitably, the overall appearance of said plant is substantially similar or visually indistinguishable to the control plant after a period, such as but not limited to three months after field transplant or 36 days after topping. Preferably, (i) the stalk height of the mutant, non-naturally occurring or transgenic tobacco plants is substantially the same as the stalk height of the control tobacco plants after a period, such as but not limited to three months after field transplant or 36 days after topping; (ii) the chlorophyll content of the mutant, non-naturally occurring or transgenic tobacco plants is substantially the same as the chlorophyll content of the control tobacco plants after a period, such as but not limited to three months after field transplant or 36 days after topping; or both (i) and (ii).

Suitably, the threonine concentration in a part of the plant (for example, the leaves) is increased as compared to the control plant; and preferably, wherein (a) the methionine concentration in the part of the plant (for example, the leaves) is at least about 0.03 mg/g; (b) the threonine concentration in leaves is at least about 0.5 mg/g; (c) the methional concentration in smoke or aerosol upon heating is at least about 2000.1 µg/g; or a combination of two or more of (a), (b) and (c).

Biomass, seed or leaves comprising cells or tissue from the mutant non-naturally occurring plant or transgenic plant described herein is also provided. Tobacco product comprising a part of the mutant non-naturally occurring plant or transgenic plant, its biomass, or its leaves, or a combination thereof, as described herein, are also provided.

In a further aspect, there is provided a method for producing methional comprising the steps of: (a) providing part of a mutant, non-naturally occurring or transgenic tobacco plant; biomass, seed or leaves; or the tobacco product described herein; and (b) providing heat thereto.

In a further aspect there is provided a method for identifying tobacco material that releases elevated levels of methional into an aerosol upon heating, comprising the steps of: (a) preparing a sample of tobacco material; (b) determining the molecular mass profile of the sample; and (c) comparing the molecular mass profile at one or more of a mass:charge ratio; wherein increases at specific mass:charge ratios as compared to a control plant is indicative that the levels of methional in the aerosol will be elevated.

Tobacco material identified or identifiable by this method is also provided in a further aspect of the disclosure.

Further aspects of the present invention are set forth below.

A chimeric gene comprising the polynucleotide operably linked to one or more regulatory sequences.

A NtTS polynucleotide construct comprising, consisting or consisting essentially of at least 15-30 nucleotides, 30-50 nucleotides, 50-100 nucleotides, 100-150 nucleotides, 150-200 nucleotides, 200-300 nucleotides, 300-400 nucleotides, 400-500 nucleotides, 500-600 nucleotides or 600-700 nucleotides.

A consumable product incorporating or utilising plant material, biomass, seed or leaves according to the present invention.

A cell line comprising the (for example, one or more, two or more, three or more or four or more) isolated polynucleotide, the chimeric gene, the polynucleotide construct, the double-stranded RNA, the conjugate or the expression vector and the like according to the present invention.

A method for modulating the expression of NtTS DNA or the activity of the protein encoded thereby in a cell, said method comprising administering the (for example, one or more, two or more, three or more or four or more) chimeric gene, the polynucleotide construct, the double-stranded RNA, the conjugate or the expression vector according to the present invention.

A method for detecting, isolating, amplifying or analysing an NtTS polynucleotide, the method comprising the step of providing a sample comprising a polynucleotide and hybridising said polynucleotide to a polynucleotide molecule comprising a nucleotide sequence of at least 10 contiguous nucleotides from the isolated nucleotide sequence according to the present invention.

Use of agent that modulates the expression of NtTS DNA and the activity of the protein encoded thereby or the activity of the protein encoded thereby for reducing the methionine content in at least a part of a plant by at least 5% as compared to a control plant.

The method or the use according to the present invention, wherein the agent is or is derived from NtTS DNA, a chimeric NtTS gene, a polynucleotide construct comprising NtTS polynucleotide, an antisense RNA, a double-stranded RNA, a cDNA, a conjugate comprising NtTS polynucleotide and at least one non-nucleotide or non-polynucleotide moiety covalently attached thereto, a ribozyme, a mutagen, a zinc finger, a small molecule or a meganuclease.

In another embodiment, the polynucleotide fragment(s) encodes an antisense nucleic acid, a ribozyme, an RNA that effects spliceosome-mediated trans-splicing, an interfering RNA (RNAi), a guide RNA, or other non-translated RNA and the like. In another embodiment, the polynucleotide fragment(s) encodes an RNAi.

In a further aspect, there is provided a method of producing a tobacco product comprising the steps of: (a) obtaining seed from the mutant, non-naturally occurring or transgenic tobacco plant; (b) planting and growing the seed into a plant; (c) harvesting the plant; and (d) preparing a tobacco product from the harvested plant.

The above-mentioned embodiments are disclosed as embodiments of each of the aspects described above.

BRIEF DESCRIPTION OF THE DRAWING

FIG. 1 illustrates the LC-MS profiles of cured leaves of VC-4, TN90-4, NtTS1-3, NtTS2-3, NtTS3-2, after extraction with methanol and separation on a WatersXBridge Shield RP18 column. VC-4 is a vector-only control plant; TN90 is a non-modified tobacco plant which provides the background; NtTS1-3, NtTS2-3 and NtTS3-2 are *Nicotiana tabacum* plants which have a RNAi silenced threonine synthase gene. The arrows indicate the peaks at about 5, 9 17 and 19 minutes.

DEFINITIONS

The technical terms and expressions used within the scope of this application are generally to be given the meaning commonly applied to them in the pertinent art of plant and molecular biology. All of the following term definitions apply to the complete content of this application. The word "comprising" does not exclude other elements or steps, and the indefinite article "a" or "an" does not exclude a plurality. A single step may fulfil the functions of several features recited in the claims. The terms "about", "essentially" and "approximately" in the context of a given numerate value or range refers to a value or range that is within 20%, within 10%, or within 5%, 4%, 3%, 2% or 1% of the given value or range.

The term "isolated" refers to any entity that is taken from its natural milieu, but the term does not connote any degree of purification.

A "vector" refers to a nucleic acid vehicle that comprises a combination of nucleic acid components for enabling the transport of nucleic acid, nucleic acid constructs and nucleic acid conjugates and the like. Suitable vectors include episomes capable of extra-chromosomal replication such as circular, double-stranded DNA plasmids; linearized double-stranded DNA plasmids; and other vectors of any origin.

An "expression vector" is a nucleic acid vehicle that comprises a combination of DNA components for enabling the expression of nucleic acid, nucleic acid constructs and nucleic acid conjugates and the like. Suitable expression vectors include episomes capable of extra-chromosomal replication such as circular, double-stranded DNA plasmids; linearized double-stranded DNA plasmids; and other functionally equivalent expression vectors of any origin. An expression vector comprises at least a promoter positioned upstream and operably-linked to a nucleic acid, nucleic acid constructs or nucleic acid conjugate, as defined below.

The term "construct" refers to a double-stranded, recombinant DNA fragment comprising one or more polynucleotide. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

A "promoter" refers to a nucleic acid element/sequence, typically positioned upstream and operably-linked to a double-stranded DNA fragment. Promoters can be derived entirely from regions proximate to a native gene of interest, or can be composed of different elements derived from different native promoters or synthetic DNA segments.

The terms "homology, identity or similarity" refer to the degree of sequence similarity between two polypeptides or between two nucleic acid molecules compared by sequence alignment. The degree of homology between two discrete nucleic acid sequences being compared is a function of the number of identical, or matching, nucleotides at comparable positions. The percent identity may be determined by visual inspection and mathematical calculation. Alternatively, the percent identity of two nucleic acid sequences may be determined by comparing sequence information using a computer program such as—ClustalW, BLAST, FASTA or Smith-Waterman.

The term "plant" refers to any plant at any stage of its life cycle or development, and its progenies. In one embodiment, the plant is a tobacco plant, which refers to a plant belonging to the genus *Nicotiana*. Preferred species, cultivars, hybrids, and varieties of tobacco plant are described herein.

A "plant cell" refers to a structural and physiological unit of a plant. The plant cell may be in the form of a protoplast without a cell wall, an isolated single cell or a cultured cell, or as a part of a higher organized unit such as but not limited to, plant tissue, a plant organ, or a whole plant.

The term "plant material" refers to any solid, liquid or gaseous composition, or a combination thereof, obtainable from a plant, including biomass, leaves, leaf lamina, midrib, stems, roots, flowers or flower parts, fruits, pollen, egg cells, zygotes, seeds, cuttings, secretions, extracts, cell or tissue cultures, or any other parts or products of a plant. In one embodiment, the plant material comprises or consists of biomass, seed or leaves. In another embodiment, the plant material comprises or consists of leaves.

The term "variety" refers to a population of plants that share constant characteristics which separate them from other plants of the same species. While possessing one or more distinctive traits, a variety is further characterized by a very small overall variation between individuals within that variety. A variety is often sold commercially.

The term "line" or "breeding line" as used herein denotes a group of plants that are used during plant breeding. A line is distinguishable from a variety as it displays little variation between individuals for one or more traits of interest, although there may be some variation between individuals for other traits.

The term "reduce" or "reduced" as used herein, refers to a reduction of from about 10% to about 99%, from about 10% to about 95% or less, from about 10% to about 90% or less or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity, and/or protein expression.

The term "inhibit" or "inhibited" as used herein, refers to a reduction of from about 98% to about 100%, or a reduction of at least 98%, at least 99%, but particularly of 100%, of a quantity or an activity, such as but not limited to polypeptide activity, transcriptional activity, and/or protein expression.

The term "increase" or "increased" as used herein, refers to an increase of from about 10% to about 99%, or an increase of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100%, 200%, 300%, 400% or 500% or more of a quantity or an activity, such as but not limited to polypeptide activity, transcriptional activity, and/or protein expression.

The term "control" in the context of a control plant or control plant cells means a plant or plant cells in which the expression or activity of threonine synthase has not been modified (for example, increased or reduced) and so it can provide a comparison with a plant in which the expression or activity of threonine synthase has been modified. The control plant may comprise an empty vector. The control plant may correspond to a wild-type plant.

DETAILED DESCRIPTION

In one aspect, there is provided an isolated polynucleotide comprising, consisting or consisting essentially of a polynucleotide sequence and having at least 60% sequence identity to any of the sequences described herein, including any of polynucleotides shown in the sequence lisiting. Suitably, the isolated polynucleotides comprise, consist or consist essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto.

In one embodiment, there is provided an isolated polynucleotide comprising, consisting or consisting essentially of a polynucleotide sequence encoding a threonine synthase and having at least 90% sequence identity to SEQ ID No.1, SEQ ID No. 2 and/or SEQ ID No. 3. Suitably, the isolated polynucleotides comprise, consist or consist essentially of a sequence having at least 91%, 92%, 93%, 94%, 95%, 96%, 97%, 98%, 99% or 100% sequence identity to SEQ ID No. 1, SEQ ID No. 2 or SEQ ID No. 3. SEQ ID NO: 1 is a DNA sequence of threonine synthase from N. tabacum. SEQ ID NO:2 is a DNA sequence of threonine synthase amplified by reverse transcriptase (RT)-PCR from isolated RNA from N. tabacum (variety Hicks Broad Leaf) and sequenced. This sequence is present in one of the two ancestors of N. tabacum, Nicotiana sylvestris, as demonstrated by RT-PCR analyses. SEQ ID NO:3 is a DNA sequence of threonine synthase amplified by RT-PCR from RNA isolated from N. tabacum (variety Hicks Broad Leaf).

In another embodiment, there is provided an isolated polynucleotide comprising, consisting or consisting essentially of a polynucleotide sequence encoding a threonine synthase and having at least 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID No. 4 or SEQ ID No. 5. SEQ ID NO:4 corresponds to the genomic DNA sequence of SEQ ID NO:3. Compared to SEQ ID NO:1 the intron of 137 bp is located at position 234 from the ATG start codon. SEQ ID NO:5 corresponds to the genomic DNA sequence of threonine synthase from N. tomentosiformis.

In another embodiment, there is provided an isolated polynucleotide comprising, consisting or consisting essentially of a polynucleotide sequence encoding a threonine synthase and having at least 60%, 65%, 70%, 75%, 80%, 85%, 86%, 87%, 88%, 89% or 90 sequence identity to SEQ ID No.20. Suitably, the isolated polynucleotides comprises, consists or consists essentially of a sequence having at least 90%, 91%, 92%, 93%, 94%, 95%, 96%, 97%, 98%, 99% or 100% sequence identity to SEQ ID No.20. SEQ ID NO: 20 is a DNA sequence of threonine synthase from N. tabacum and has 85% sequence identity with SEQ ID No.1, 86% sequence identity with SEQ ID No.2, and 86% sequence identity with SEQ ID No.3.

The term "NtTS polynucleotide" relates to polynucleotides encoding threonine synthase from Nicotiana tabacum comprising, consisting or consisting essentially of polynucleotides with substantial homology (that is, sequence similarity) or substantial identity to SEQ ID NO:1, SEQ ID NO:2, SEQ ID NO:3, SEQ ID NO:4, SEQ ID NO:5 or SEQ ID NO:20; fragments of the NtTS polynucleotide including fragments of SEQ ID NO:1, SEQ ID NO:2, SEQ ID NO:3, SEQ ID NO:4 SEQ ID NO:5 or SEQ ID NO:20; and fragments of SEQ ID NO:1, SEQ ID NO:2, SEQ ID NO:3, SEQ ID NO:4, SEQ ID NO:5 or SEQ ID NO:20 with substantial homology (that is, sequence similarity) or substantial identity thereto that have at least about 60%, 65%, 70%, 75%, 80%, 85%, 87%, 88%, 89%, 90%, 91%, 92%, 93%, 94%, 95% 96%, 97%, 98%, or 99% or 100% sequence identity to the corresponding fragments of SEQ ID NO:1, SEQ ID NO:2, SEQ ID NO:3, SEQ ID NO:4, SEQ ID NO:5 or SEQ ID NO:20. Exemplary fragments are set forth in SEQ ID Nos 9 to 19. As described herein, the variant may have at least about 60%, 65%, 70%, 75%, 80%, 85%, 86%, 87%, 88%, 89%, 90%, 91%, 92%, 93%, 94%, 95% 96%, 97%, 98%, or 99% sequence identity to the sequence of SEQ ID NO:1, SEQ ID NO:2, SEQ ID NO:3, SEQ ID NO:4, SEQ ID NO:5 or SEQ ID NO:20. The NtTS polynucleotide also includes sequences comprising a sufficient or substantial degree of identity or similarity to SEQ ID NO:1, SEQ ID NO:2, SEQ ID NO:3, SEQ ID NO:4, SEQ ID NO:5 or SEQ ID NO:20 to encode a polypeptide that functions as a threonine synthase. In one embodiment, the term "NtTS polynucleotide" refers to a polymer of nucleotides which comprises, consists or consists essentially of a polynucleotide designated herein as SEQ ID NO:1, SEQ ID NO:2, SEQ ID NO:3, SEQ ID NO:4, SEQ ID NO:5 or SEQ ID NO:20.

The term "polynucleotide" refers to a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof.

A polynucleotide as described herein will generally contain phosphodiester bonds, although in some cases, polynucleotide analogs are included that may have alternate backbones, comprising, for example, phosphoramidate, phosphorothioate, phosphorodithioate, or O-methylphosphoroamidite linkages; and peptide polynucleotide backbones and linkages. Other analog polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogs can be made; alternatively, mixtures of different polynucleotide analogs, and mixtures of naturally occurring polynucleotides and analogs may be made.

A variety of polynucleotide analogs are known, including, for example, phosphoramidate, phosphorothioate, phosphorodithioate, O-methylphosphoroamidite linkages and peptide polynucleotide backbones and linkages. Other analog polynucleotides include those with positive backbones, non-ionic backbones and non-ribose backbones. Polynucleotides containing one or more carbocyclic sugars are also included.

Other analogs include peptide polynucleotides (PNA) which are peptide polynucleotide analogs. These backbones are substantially non-ionic under neutral conditions, in contrast to the highly charged phosphodiester backbone of naturally occurring polynucleotides. This may result in advantages. First, the PNA backbone may exhibit improved hybridization kinetics. PNAs have larger changes in the melting temperature (Tm) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs may not be degraded or degraded to a lesser extent by cellular enzymes, and thus may be more stable.

Among the uses of the disclosed polynucleotides, and combinations of fragments thereof, is the use of fragments as probes in nucleic acid hybridization assays or primers in nucleic acid amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Thus, in one aspect, there is also provided a method for detecting NtTS polynucleotides comprising the use of the probes and/or the primers. Exemplary primers are set forth in SEQ ID NOs: 10 to 14. Optionally, said primers may be used as probes. Exemplary primers or probes may hybridise to regions that are homologous between SEQ ID NOs: 1, 2 and 3 or SEQ ID NO:20. Exemplary primers or probes may hybridise to nucleotides 1-46 of SEQ ID NOs: 1, 2 and 3; to nucleotides 1-52 of SEQ ID NO:20; to nucleotides 99-141 of SEQ ID NO:1; to nucleotides 102-144 of SEQ ID NO: 2 and SEQ ID NO:3; to nucleotides 102-153 of SEQ ID NO:20; to nucleotides 1325-1362 of SEQ ID NOs: 1, 2 and 3; or to nucleotides 1334-1371 of SEQ ID NO:20.

The basic parameters affecting the choice of hybridization conditions and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the amino acid sequences described herein, sets of degenerate oligonucleotides can be prepared. Such oligonucleotides are useful as primers, for example, in polymerase chain reactions (PCR), whereby DNA fragments are isolated and amplified. In certain embodiments, degenerate primers can be used as probes for genetic libraries. Such libraries would include but are not limited to cDNA libraries, genomic libraries, and even electronic EST (express sequence tag) or DNA libraries. Homologous sequences identified by this method would then be used as probes to identify homologues of the NtTS sequences identified herein.

Also of potential use are polynucleotides and oligonucleotides (for example, primers or probes) that hybridize under reduced stringency conditions, typically moderately stringent conditions, and commonly highly stringent conditions to an NtTS polynucleotide as described herein. The basic parameters affecting the choice of hybridization conditions and guidance for devising suitable conditions are set forth by Sambrook et al. (1989, Molecular Cloning: A Laboratory Manual, Cold Spring Harbor, N.Y.)., and can be readily determined by those having ordinary skill in the art based on, for example, the length or base composition of the polynucleotide.

One way of achieving moderately stringent conditions involves the use of a prewashing solution containing 5× Standard Sodium Citrate, 0.5% Sodium Dodecyl Sulphate, 1.0 mM Ethylenediaminetetraacetic acid (pH 8.0), hybridization buffer of about 50% formamide, 6× Standard Sodium Citrate, and a hybridization temperature of about 55° C. (or other similar hybridization solutions, such as one containing about 50% formamide, with a hybridization temperature of about 42° C.), and washing conditions of about 60° C., in 0.5× Standard Sodium Citrate, 0.1% Sodium Dodecyl Sulphate. Generally, highly stringent conditions are defined as hybridization conditions as above, but with washing at approximately 68° C., 0.2× Standard Sodium Citrate, 0.1% Sodium Dodecyl Sulphate. SSPE (1×SSPE is 0.15M sodium chloride, 10 mM sodium phosphate, and 1.25 mM Ethylenediaminetetraacetic acid, pH 7.4) can be substituted for Standard Sodium Citrate (1× Standard Sodium Citrate is 0.15M sodium chloride and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook et al., supra). When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature ($T_m$) of the hybrid, where $T_m$ is determined according to the following equations. For hybrids less than 18 base pairs in length, $T_m$ (° C.)=2(number of A+T bases)+4(number of G+C bases). For hybrids above 18 base pairs in length, $T_m$ (° C.)=81.5+16.6(log 10 [Na+])+0.41(% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 70%, 75%, 80%, 85%, 90%, 95%, 96%, 97%, 98%, 99% or 100%) with a polynucleotide to which it hybridizes.

As will be understood by the person skilled in the art, a linear DNA has two possible orientations: the 5'-to-3' direction and the 3'-to-5' direction. For example, if a reference sequence is positioned in the 5'-to-3' direction, and if a second sequence is positioned in the 5'-to-3' direction within the same polynucleotide molecule/strand, then the reference sequence and the second sequence are orientated in the same direction, or have the same orientation. Typically, a promoter sequence and a gene of interest under the regulation of the given promoter are positioned in the same orientation. However, with respect to the reference sequence positioned in the 5'-to-3' direction, if a second sequence is positioned in the 3'-to-5'direction within the same polynucleotide molecule/strand, then the reference sequence and the second sequence are orientated in anti-sense direction, or have anti-sense orientation. Two sequences having anti-sense orientations with respect to each other can be alternatively described as having the same orientation, if the reference sequence (5'-to-3' direction) and the reverse complementary sequence of the reference sequence (reference sequence positioned in the 5'-to-3') are positioned within the same polynucleotide molecule/strand. The sequences set forth herein are shown in the 5'-to-3' direction.

Recombinant constructs provided herein can be used to transform plants or plant cells in order to modulate NtTS protein expression levels. A recombinant polynucleotide construct can comprise a polynucleotide encoding a NtTS polynucleotide as described herein, operably linked to a regulatory region suitable for expressing the NtTS polypeptide in the plant or cell. Thus, a polynucleotide can comprise a coding sequence that encodes the NtTS polypeptide as described herein.

The NtTS polypeptide encoded by a recombinant polynucleotide can be a native NtTS polypeptide, or can be heterologous to the cell. In some cases, the recombinant construct contains a polynucleotide that reduces or inhibits expression of a NtTS-modulating polypeptide, operably linked to a regulatory region. Examples of suitable regulatory regions are described herein.

Vectors containing recombinant polynucleotide constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available.

The vectors can also include, for example, origins of replication, scaffold attachment regions (SARs) or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase (GUS), green fluorescent protein (GFP), glutathione S-transferase (GST), polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. Stably transformed cells typically retain the introduced polynucleotide with each cell division. A plant or plant cell may also be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions.

A number of methods are available in the art for transforming a plant cell which are all encompassed herein, including biolistics, gene gun techniques, *Agrobacterium*-mediated transformation, viral vector-mediated transformation and electroporation. The *Agrobacterium* system for integration of foreign DNA into plant chromosomes has been extensively studied, to modified, and exploited for plant genetic engineering. Naked recombinant DNA molecules comprising DNA sequences corresponding to the subject purified tobacco protein operably linked, in the sense or antisense orientation, to regulatory sequences are joined to appropriate T-DNA sequences by conventional methods. These are introduced into tobacco protoplasts by polyethylene glycol techniques or by electroporation techniques, both of which are standard. Alternatively, such vectors comprising recombinant nucleic acid molecules encoding the subject purified tobacco protein are introduced into live *Agrobacterium* cells, which then transfer the nucleic acid into the plant cells. Transformation by naked DNA without accompanying T-DNA vector sequences can be accomplished via fusion of tobacco protoplasts with DNA-containing liposomes or via electroporation. Naked DNA unaccompanied by T-DNA vector sequences can also be used to transform tobacco cells via inert, high velocity micropro-jectiles.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Suitable promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of suitable promoters for controlling NtTS RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters.

Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistils, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Suitable leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Suitable senescence-specific promoters include a tomato promoter active during fruit ripening, senescence and abscission of leaves, a maize promoter of gene encoding a cysteine protease. Suitable anther-specific promoters can be used. Suitable root-preferred promoters known to persons skilled in the art may be selected. Suitable seed-preferred promoters include both seed-specific promoters (those promoters active during seed development such as promoters of seed storage proteins) and seed-germinating promoters (those promoters active during seed germination). Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40; nucic; and celA (cellulose synthase). Gamma-zein is an endosperm-specific promoter. Glob-1 is an embryo-specific promoter. For dicots, seed-specific promoters include, but are not limited to, bean beta-phaseolin, napin, β-conglycinin, soybean lectin, cruciferin, and the like. For monocots, seed-specific promoters include, but are not limited to, a maize 15 kDa zein promoter, a 22 kDa zein promoter, a 27 kDa zein promoter, a g-zein promoter, a 27 kDa γ-zein promoter (such as gzw64A promoter, see Genbank Accession number S78780), a waxy promoter, a shrunken 1 promoter, a shrunken 2 promoter, a globulin 1 promoter (see Genbank Accession number L22344), an ltp2 promoter, cim1 promoter, maize end1 and end2 promoters, nuc1 promoter, Zm40 promoter, eep1 and eep2; lec1, thioredoxin H promoter; mlip15 promoter, PCNA2 promoter; and the shrunken-2 promoter.

Examples of inducible promoters include promoters responsive to pathogen attack, anaerobic conditions, elevated temperature, light, drought, cold temperature, or high salt concentration. Pathogen-inducible promoters include those from pathogenesis-related proteins (PR proteins), which are induced following infection by a pathogen (for example, PR proteins, SAR proteins, beta-1,3-glucanase, chitinase).

In addition to plant promoters, other suitable promoters may be derived from bacterial origin for example, the octopine synthase promoter, the nopaline synthase promoter and other promoters derived from Ti plasmids), or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

The term "NtTS polypeptide" refers to a polypeptide encoding threonine synthase from *Nicotiana tabacum* and includes polypeptides comprising, consisting or consisting essentially of an amino acid sequence encoded by a polynucleotide with at least about 60%, 65%, 70%, 75%, 80%, 85%, 86%, 87%, 88%, 89%, 90%, 91%, 92%, 93%, 94%, 95% 96%, 97%, 98%, 99% or 100% sequence identity to SEQ ID NO:1, SEQ ID NO:2, or SEQ ID NO:3, or a polynucleotide with at least about 60%, 65%, 70%, 75%, 80%, 85%, 86%,87%, 88%, 89%, 90%, 91%, 92%, 93%, 94%, 95% 96%, 97%, 98%, 99% or 100% sequence identity to SEQ ID NO:4, SEQ ID NO:5 or SEQ ID NO:20; fragments of the NtTS polynucleotide of SEQ ID NO:1, SEQ ID NO:2, SEQ ID NO:3, SEQ ID NO:4, SEQ ID NO:5 or SEQ ID NO:20; and fragments of SEQ ID NO:1, SEQ ID NO:2, SEQ ID NO:3, SEQ ID NO:4, SEQ ID NO:5 or SEQ ID NO:20 that have at least about 60%, 65%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NO:1, SEQ ID NO:2, SEQ ID NO:3, SEQ ID NO:4, SEQ ID NO:5 or SEQ ID NO:20. Exemplary fragments are set forth in SEQ ID Nos 9 to 19. The NtTS polypeptides also include sequences comprising a sufficient or substantial degree of identity or similarity to SEQ ID NO:6, SEQ ID NO:7, or SEQ ID NO:8 to function as a threonine synthase and include sequences with at least 95% sequence identity to SEQ ID NO:6, SEQ ID NO:7, SEQ ID NO:8 or SEQ ID NO:21. SEQ ID NO. 6 is the translated sequence of SEQ ID NO: 1. SEQ ID NO:7 is the translated sequence of SEQ ID NO: 2. SEQ ID NO:8 is the translated sequence of SEQ ID NO. 3. SEQ ID NO:21 is the translated sequence of SEQ ID NO:20 and has 89% sequence identity to SEQ ID NO:7, SEQ ID NO:8 or SEQ ID NO:9.

In one embodiment, the fragments of the NtTS polypeptides retain threonine synthase activity. NtTS polypeptides also include variants and mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally provided that they still function as a threonine synthase. NtTS polypeptides may be in linear form or cyclized using known methods. The term "NtTS polypeptide" can refer to a polypeptide comprising, consisting or consisting essentially of the sequence set forth in SEQ ID NO:6, SEQ ID NO:7, SEQ ID NO:8 or SEQ ID NO:21.

In another aspect, there is provided an isolated polypeptide comprising, consisting or consisting essentially of a polypeptide sequence having at least 60% sequence identity to any of the sequences described herein, including any of polypeptides shown in the sequence listing. Suitably, the isolated polypeptides comprise, consist or consist essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto.

NtTS polypeptides include variants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. The variant may have alterations which produce a silent change and result in a functionally equivalent protein. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below. Amino acids in the same block in the second column and preferably in the same line in the third column may be substituted for each other:

| ALIPHATIC | Non-polar | Gly Ala Pro |
| | | Ile Leu Val |
| | Polar - uncharged | Cys Ser Thr Met |
| | | Asn Gly |
| | Polar - charged | Asp Glu |
| | | Lys Arg |
| AROMATIC | | His Phe TrpTyr |

The NtTS polypeptide may be a mature protein or an immature protein or a protein derived from an immature protein. NtTS polypeptides may be in linear form or cyclized using known methods. NtTS polypeptides comprise at least 10, at least 20, at least 30, or at least 40 contiguous amino acids.

In one embodiment, there is provided an isolated polypeptide encoded by any one of the polynucleotides comprising, consisting or consisting essentially of a sequence encoding a threonine synthase and having at least 60%, 65%, 70%, 75%, 80%, 85%, 86%, 87%, 88%, 89%, 90%, 95%, 96%, 97%, 98%, 99% or 100% sequence identity to SEQ ID No. 1, SEQ ID No. 2 or SEQ ID No. 3 or by any one of the polynucleotides comprising, consisting or consisting essentially of a sequence having at least 60%, 65%, 70%, 75%, 80%, 85%, 86%, 87%, 88%, 89%, 90%, 91%, 92%, 93%, 94%, 95%, 96%, 97%, 98% or 100% sequence identity to SEQ ID No. 4, SEQ ID No. 5 or SEQ ID NO:20.

In another embodiment, there is provided an isolated polypeptide encoding a threonine synthase and comprising, consisting or consisting essentially of a polypeptide sequence having at least 60%, 65%, 70%, 75%, 80%, 85%, 86%, 87%, 88%, 89% 90%, 91%, 92%, 93%, 94%, 95%, 96%, 97%, 98%, 99% or 100% sequence identity to the sequence set forth in SEQ ID NO: 6, SEQ ID NO: 7, SEQ ID NO:8 or SEQ ID NO:21.

In another embodiment, there is provided an isolated polypeptide encoded encoding a threonine synthase and comprising, consisting or consisting essentially of the sequence set forth in SEQ ID NO: 6, SEQ ID NO: 7, SEQ ID NO:8 or SEQ ID NO:21.

Fragments of the polypeptide sequences are also disclosed herein, suitably, such fragments retain threonine synthase activity.

Mutant polypeptide variants can be used to create mutant plants, non-naturally occurring plants, or transgenic plants comprising the mutant NtTS polypeptide. Suitably, the mutant NtTS polypeptide retain threonine synthase activity.

A polypeptide may be prepared by culturing transformed or recombinant host cells under culture conditions suitable to express a polypeptide. The resulting expressed polypeptide may then be purified from such culture using known purification processes. The purification of the polypeptide may include an affinity column containing agents which will bind to the polypeptide; one or more column steps over such affinity resins; one or more steps involving hydrophobic interaction chromatography; or immunoaffinity chromatography. Alternatively, the polypeptide may also be expressed in a form that will facilitate purification. For example, it may be expressed as a fusion polypeptide, such as those of maltose binding polypeptide (MBP), glutathione-S-transferase (GST) or thioredoxin (TRX). Kits for expression and purification of fusion polypeptides are commercially available. The polypeptide may be tagged with an epitope and subsequently purified by using a specific antibody directed to such epitope. One or more liquid chromatography steps—such as reverse-phase high performance liquid chromatography can be employed to further purify the polypeptide. Some or all of the foregoing purification steps, in various combinations, can be employed to provide a substantially homogeneous recombinant polypeptide. The polypeptide thus purified may be substantially free of other polypeptides and is defined herein as an "substantially purified polypeptide"; such purified polypeptides include NtTS polypeptides, fragments, variants, and the like. Expression, isolation, and purification of the polypeptides and fragments can be accomplished by any suitable technique, including but not limited to the methods described herein.

It is also possible to utilise an affinity column such as a monoclonal antibody generated against polypeptides, to affinity-purify expressed polypeptides. These polypeptides can be removed from an affinity column using conventional techniques, for example, in a high salt elution buffer and then dialyzed into a lower salt buffer for use or by changing pH or other components depending on the affinity matrix utilized, or be competitively removed using the naturally occurring substrate of the affinity moiety.

A polypeptide may also be produced by known conventional chemical synthesis. Methods for constructing the polypeptides or fragments thereof by synthetic means are known to those skilled in the art. The synthetically-constructed polypeptide sequences, by virtue of sharing primary, secondary or tertiary structural or conformational characteristics with a native polypeptides may possess biological properties in common therewith, including biological activity.

The term 'non-naturally occurring' as used herein describes an entity (for example, a polynucleotide, a genetic mutation, a polypeptide, a plant, a plant cell and plant material) that is not formed by nature or that does not exist in nature. Such non-naturally occurring entities or artificial entities may be made, synthesized, initiated, modified, intervened, or manipulated by methods described herein or that are known in the art. Thus, by way of example, a non-naturally occurring plant, a non-naturally occurring plant cell or non-naturally occurring plant material may be made using traditional plant breeding techniques—such as back-crossing—or by genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell. Differences in genetic background can be detected by phenotypic differences or by molecular biology techniques known in the art—such as nucleic acid sequencing, presence or absence of genetic markers (for example, microsatellite RNA markers).

In another embodiment, antibodies that are immunoreactive with the NtTS polypeptides are provided herein. The NtTS polypeptides, fragments, variants, fusion polypeptides, and the like, as set forth herein, can be employed as "immunogens" in producing antibodies immunoreactive therewith. Such antibodies may specifically bind to the NtTS polypeptides via the antigen-binding sites of the antibody. Specifically binding antibodies are those that will specifically recognize and bind with NtTS family polypeptides, homologues, and variants, but not with other molecules. In one embodiment, the antibodies are specific for polypeptides having an NtTS amino acid sequence as set forth herein and do not cross-react with other polypeptides.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides can be prepared by conventional techniques. Hybridoma cell lines that produce monoclonal antibodies specific for the polypeptides are also contemplated herein. Such hybridomas can be produced and identified by conventional techniques. For the production of antibodies, various host animals may be immunized by injection with an NtTS polypeptide, fragment, variant, or mutants thereof. Such host animals may include, but are not limited to, rabbits, mice, and rats, to name a few. Various adjutants may be used to increase the immunological response. Depending on the host species, such adjuvants include, but are not limited to, Freund's (complete and incomplete), mineral gels such as aluminium hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

The antibodies can also be used in assays to detect the presence of the polypeptides or fragments, either in vitro or in vivo. The antibodies also can be employed in purifying polypeptides or fragments by immunoaffinity chromatography.

Compositions that can reduce the expression or the activity of threonine synthase include, but are not limited to, sequence-specific polynucleotides that can interfere with the transcription of one or more endogenous threonine synthase gene(s); sequence-specific polynucleotides that can interfere with the translation of threonine synthase RNA transcripts (for example, double-stranded RNAs, microRNA, siRNAs, ribozymes); sequence-specific polypeptides that can interfere with the stability of threonine synthase proteins; sequence-specific polynucleotides that can interfere with the enzymatic activity of threonine synthase protein or the binding activity of threonine synthase protein with respect to substrates or regulatory proteins; antibodies that exhibit specificity for threonine synthase protein; small molecule compounds that can interfere with the stability of threonine synthase protein or the enzymatic activity of threonine synthase protein or the binding activity of threonine synthase protein; zinc finger proteins that bind threonine synthase polynucleotide; and meganucleases that have activity towards threonine synthase polynucleotide.

Antisense technology is one well-known method that can be used to modulate (for example, reduce or inhibit) the expression of a NtTS polypeptide. A polynucleotide of the NtTS gene to be repressed is cloned and operably linked to a regulatory region and a transcription termination sequence so that the antisense strand of RNA is transcribed. The recombinant construct is then transformed into plants and the antisense strand of RNA is produced. The polynucleotide need not be the entire sequence of the gene to be repressed, but typically will be substantially complementary to at least a portion of the sense strand of the gene to be repressed (regardless of whether it is in the coding or non-coding region).

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5-UG-3' nucleotide sequence. The construction and production of hammerhead ribozymes is known in the art. Hammerhead ribozyme sequences can be embedded in a stable RNA such as a transfer RNA (tRNA) to increase cleavage efficiency in vivo.

In one embodiment, the sequence-specific polynucleotides that can interfere with the translation of threonine synthase RNA transcript(s) is RNAi. RNA interference ("RNAi") or RNA silencing is an evolutionarily conserved process by which specific mRNAs can be targeted for enzymatic degradation. A double-stranded RNA (double-stranded RNA) must be introduced or produced by a cell (for example, double-stranded RNA virus, or NtTS RNAi polynucleotides) to initiate the RNAi pathway. The double-stranded RNA can be converted into multiple siRNA duplexes of 21-23 bp length ("siRNAs") by RNases III, which are double-stranded RNA-specific endonucleases ("Dicer"). The siRNAs can be subsequently recognized by RNA-induced silencing complexes ("RISC") that promote the unwinding of siRNA through an ATP-dependent process. The unwound antisense strand of the siRNA guides the activated RISC to the targeted mRNA (for example, NtTS RNA variants) comprising a sequence complementary to the siRNA anti-sense strand. The targeted mRNA and the antisense strand can form an A-form helix, and the major groove of the A-form helix can be recognized by the activated RISC. The target mRNA can be cleaved by activated RISC at a single site defined by the binding site of the 5'-end of the siRNA strand. The activated RISC can be recycled to catalyze another cleavage event.

NtTS RNAi expression vectors may comprise NtTS RNAi constructs encoding NtTS RNAi polynucleotides that exhibit RNA interference activity by reducing the expression level of NtTS mRNAs, NtTS pre-mRNAs, or related NtTS RNA variants. The expression vectors may comprise a promoter positioned upstream and operably-linked to a NtTS RNAi construct, as further described herein. NtTS RNAi expression vectors may comprise a suitable minimal core promoter, a NtTS RNAi construct of interest, an upstream (5') regulatory region, a downstream (3') regulatory region, including transcription termination and polyadenylation signals, and other sequences known to persons skilled in the art, such as various selection markers.

The NtTS polynucleotides can be produced in various forms, including as double stranded structures (that is, a double-stranded RNA molecule comprising an antisense strand and a complementary sense strand), double-stranded hairpin-like structures ("dsRNAi"), or single-stranded structures (that is, a ssRNA molecule comprising just an antisense strand). The structures may comprise a duplex, asymmetric duplex, hairpin or asymmetric hairpin secondary structure, having self-complementary sense and antisense strands. The NtTS dsRNAi can be enzymatically converted to double-stranded NtTS siRNAs. One of the strands of the NtTS siRNA duplex can anneal to a complementary sequence within the target NtTS mRNA and related NtTS RNA variants. The siRNA/mRNA duplexes are recognized by RISC that can cleave NtTS RNAs at multiple sites in a sequence-dependent manner, resulting in the degradation of the target NtTS mRNA and related NtTS RNA variants.

The double-stranded RNA molecules may include siRNA molecules assembled from a single oligonucleotide in a stem-loop structure, wherein self-complementary sense and antisense regions of the siRNA molecule are linked by means of a polynucleotide based or non-polynucleotide-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi.

The use of small hairpin RNA (shRNA) molecules is also contemplated herein and comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a double-stranded RNA molecule (optionally with additional processing steps that may result in addition or removal of one, two, three or more nucleotides from the 3' end or the 5' end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end or the 5' end of either or both strands). The spacer sequence is typically an unrelated nucleotide sequence that is situated between two complementary nucleotide sequence regions which, when annealed into a double-stranded polynucleotide, comprise a shRNA. The spacer sequence generally comprises between about 3 and about 100 nucleotides.

Any NtTS RNA polynucleotide of interest can be produced by selecting a suitable sequence composition, loop size, and stem length for producing the NtTS hairpin duplex. A suitable range for designing stem lengths of a hairpin duplex, includes stem lengths of at least about 10, 11, 12, 13, 14, 15, 16, 17, 18, 19 or 20 nucleotides—such as about 14-30 nucleotides, about 30-50 nucleotides, about 50-100 nucleotides, about 100-150 nucleotides, about 150-200 nucleotides, about 200-300 nucleotides, about 300-400 nucleotides, about 400-500 nucleotides, about 500-600 nucleotides, and about 600-700 nucleotides. A suitable range for designing loop lengths of a hairpin duplex, includes loop lengths of about 4-25 nucleotides, about 25-50 nucleotides, or longer if the stem length of the hair duplex is substantial. In certain embodiments, a double-stranded RNA (dsRNA) or single-stranded RNA (ssRNA) molecule is between about 15 and about 40 nucleotides in length. In another embodiment, the siRNA molecule is a dsRNA or ssRNA molecule between about 15 and about 35 nucleotides in length. In another embodiment, the siRNA molecule is a dsRNA or ssRNA molecule between about 17 and about 30 nucleotides in length. In another embodiment, the siRNA molecule is a dsRNA or ssRNA molecule between about 19 and about 25 nucleotides in length. In another embodiment, the siRNA molecule is a dsRNA or ssRNA molecule between about 21 to about 23 nucleotides in length. In certain embodiments, hairpin structures with duplexed regions longer than 21 nucleotides may promote effective siRNA-directed silencing, regardless of loop sequence and length.

The target mRNA sequence is typically between about 14 to about 50 nucleotides in length. The target mRNA can, therefore, be scanned for regions between about 14 and about 50 nucleotides in length that preferably meet one or more of the following criteria for a target sequence: an A+T/G+C ratio of between about 2:1 and about 1:2; an AA dinucleotide or a CA dinucleotide at the 5' end of the target sequence; a sequence of at least 10 consecutive nucleotides unique to the target mRNA (that is, the sequence is not present in other mRNA sequences from the same plant); and no "runs" of more than three consecutive guanine (G) nucleotides or more than three consecutive cytosine (C) nucleotides. These criteria can be assessed using various techniques known in the art, for example, computer programs such as BLAST can be used to search publicly available databases to determine whether the selected target sequence is unique to the target mRNA. Alternatively, a target sequence can be selected (and a siRNA sequence designed) using computer software available commercially (for example, OligoEngine, Target Finder and the siRNA Design Tool which are commercially available.

In one embodiment, target mRNA sequences are selected that are between about 14 and about 30 nucleotides in length that meet one or more of the above criteria. In another embodiment, target sequences are selected that are between about 16 and about 30 nucleotides in length that meet one or more of the above criteria. In a further embodiment, target sequences are selected that are between about 19 and about 30 nucleotides in length that meet one or more of the above criteria. In another embodiment, target sequences are selected that are between about 19 and about 25 nucleotides in length that meet one or more of the above criteria.

In an exemplary embodiment, the molecules used to modulate expression comprise a specific sequence (for example, an antisense sequence) that is complementary to at least 12, 13, 14, 15, 16, 17, 18, 19, 20, 21, 22, 23, 24, 25, 26, 27, 28, 29, 30, or more contiguous nucleotides of any one of the NtTS polynucleotide sequences described herein—such as SEQ ID NOs:1 to 5 or 20.

In a further exemplary embodiment, molecules used to modulate expression comprise a sequence (for example, an antisense sequence) that is complementary to at least 12, 13, 14, 15, 16, 17, 18, 19, 20, 21, 22, 23, 24, 25, 26, 27, 28, 29 or 30 or more contiguous nucleotides of nucleotides 1-46 of SEQ ID NOs: 1, 2 and 3; nucleotides 1-52 of SEQ ID NO:20; nucleotides 99-141 of SEQ ID NO:1; nucleotides 102-144 of SEQ ID NO: 2 and SEQ ID NO:3; nucleotides 102-153 of SEQ ID NO:20; nucleotides 1325-1362 of SEQ ID NOs: 1, 2 and 3; or nucleotides 1334-1371 of SEQ ID NO:20.

In a further exemplary embodiment, the molecules used to modulate expression comprise a sequence (for example, an antisense sequence) that is complementary to at least 12, 13, 14, 15, 16, 17, 18, 19, 20, 21, 22, 23, 24, 25, 26, 27, 28, 29 or 30 or more contiguous nucleotides of nucleotides 454-805 of SEQ ID NO:1, SEQ ID NO: 2, or SEQ ID NO:3 or nucleotides 463-814 of SEQ ID NO:20.

The specific antisense sequence comprised by the siRNA molecule can be identical or substantially identical to the complement of the target sequence. In one embodiment, the specific antisense sequence comprised by the siRNA molecule is at least about 75%, 80%, 85%, 90%, 95%, 96%, 97%, 98%, 99% or 100% identical to the complement of the target mRNA sequence. Methods of determining sequence identity are known in the art and can be determined, for example, by using the BLASTN program of the University of Wisconsin Computer Group (GCG) software or provided on the NCBI website.

The specific antisense sequence of the siRNA molecules may exhibit variability by differing (for example, by nucleotide substitution, including transition or transversion) at one, two, three, four or more nucleotides from the sequence of the target mRNA. When such nucleotide substitutions are present in the antisense strand of a double-stranded RNA molecule, the complementary nucleotide in the sense strand with which the substitute nucleotide would typically form hydrogen bond base-pairing may or may not be correspondingly substituted double-stranded RNA molecules in which one or more nucleotide substitution occurs in the sense sequence, but not in the antisense strand, are also contemplated. When the antisense sequence of an siRNA molecule comprises one or more mismatches between the nucleotide sequence of the siRNA and the target nucleotide sequence, as described above, the mismatches may be found at the 3' terminus, the 5 terminus or in the central portion of the antisense sequence.

In another embodiment, the siRNA molecules comprise a specific antisense sequence that is capable of selectively hybridizing under stringent conditions to a portion of a naturally occurring target gene or target mRNA. As known to those of ordinary skill in the art, variations in stringency of hybridization conditions may be achieved by altering the time, temperature or concentration of the solutions used for the hybridization and wash steps. Suitable conditions can also depend in part on the particular nucleotide sequences used, for example the sequence of the target mRNA or gene.

One method for inducing double stranded RNA-silencing in plants is transformation with a gene construct producing hairpin RNA (see Smith et al. (2000) *Nature*, 407, 319-320). Such constructs comprise inverted regions of the target gene sequence, separated by an appropriate spacer. The insertion of a functional plant intron region as a spacer fragment additionally increases the efficiency of the gene silencing induction, due to generation of an intron spliced hairpin RNA (Wesley at al. (2001) *Plant J.*, 27, 581-590). Suitably, the stem length is about 50 nucleotides to about 1 kilobases in length. Methods for producing intron spliced hairpin RNA are well described in the art (see for example, Bioscience, Biotechnology, and Biochemistry (2008) 72, 2, 615-617).

RNAi molecules having a duplex or double-stranded structure, for example double-stranded RNA or shRNA, can have blunt ends, or can have 3' or 5' overhangs. As used herein, "overhang" refers to the unpaired nucleotide or nucleotides that protrude from a duplex structure when a 3'-terminus of one RNA strand extends beyond the 5'-terminus of the other strand (3' overhang), or vice versa (5' overhang). The nucleotides comprising the overhang can be ribonucleotides, deoxyribonucleotides or modified versions thereof. In one embodiment, at least one strand of the RNAi molecule has a 3' overhang from about 1 to about 6 nucleotides in length. In other embodiments, the 3' overhang is from about 1 to about 5 nucleotides, from about 1 to about 3 nucleotides and from about 2 to about 4 nucleotides in length.

When the RNAi molecule comprises a 3' overhang at one end of the molecule, the other end can be blunt-ended or have also an overhang (5' or 3'). When the RNAi molecule comprises an overhang at both ends of the molecule, the length of the overhangs may be the same or different. In one embodiment, the RNAi molecule comprises 3' overhangs of about 1 to about 3 nucleotides on both ends of the molecule. In a further embodiment, the RNAi molecule is a double-stranded RNA having a 3' overhang of 2 nucleotides at both ends of the molecule. In yet another embodiment, the nucleotides comprising the overhang of the RNAi are TT dinucleotides or UU dinucleotides.

When determining the percentage identity of the RNAi molecule comprising one or more overhangs to the target mRNA sequence, the overhang(s) may or may not be taken into account. For example, the nucleotides from a 3' overhang and up to 2 nucleotides from the 5'- or 3'-terminus of the double strand may be modified without significant loss of activity of the siRNA molecule.

The RNAi molecules can comprise one or more 5' or 3'-cap structures. The RNAi molecule can comprise a cap structure at the 3'-end of the sense strand, the antisense strand, or both the sense and antisense strands; or at the 5-end of the sense strand, the antisense strand, or both the sense and antisense strands of the RNAi molecule. Alternatively, the RNAi molecule can comprise a cap structure at both the 3'-end and 5'-end of the RNAi molecule. The term "cap structure" refers to a chemical modification incorporated at either terminus of an oligonucleotide, which protects the molecule from exonuclease degradation, and may also facilitate delivery or localisation within a cell.

Another modification applicable to RNAi molecules is the chemical linkage to the RNAi molecule of one or more moieties or conjugates which enhance the activity, cellular distribution, cellular uptake, bioavailability or stability of the RNAi molecule. The polynucleotides may be synthesized or modified by methods well established in the art. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues.

In yet another embodiment, the nucleotides at one or both of the two single strands may be modified to reduce or inhibit the activation of cellular enzymes, such as, for example, without limitation, certain nucleases. Techniques for reducing or inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate. Thus, at least one 2'-hydroxyl group of the nucleotides on a double-stranded RNA is replaced by a chemical group. Also, at least one nucleotide may be modified to form a locked nucleotide. Such locked nucleotide contains a methylene or ethylene bridge that connects the 2'-oxygen of ribose with the 4'-carbon of ribose. Introduction of a locked nucleotide into an oligonucleotide improves the affinity for complementary sequences and increases the melting temperature by several degrees.

Ligands may be conjugated to a RNAi molecule, for example, to enhance its cellular absorption. In certain embodiments, a hydrophobic ligand is conjugated to the molecule to facilitate direct permeation of the cellular membrane. These approaches have been used to facilitate cell permeation of antisense oligonucleotides. In certain instances, conjugation of a cationic ligand to oligonucleotides often results in improved resistance to nucleases. Representative examples of cationic ligands include propylammonium and dimethylpropylammonium. Anti-sense oligonucleotides can retain their high binding affinity to mRNA when the cationic ligand is dispersed throughout the oligonucleotide.

The molecules and nucleotides described herein may be prepared using well-known techniques of solid-phase synthesis. Any other means for such synthesis known in the art may additionally or alternatively be employed.

Various embodiments are directed to NtTS expression vectors comprising one or more NtTS polynucleotides or NtTS RNAi constructs that comprise one or more NtTS polynucleotides. Various embodiments are directed to expression vectors comprising one or more NtTS polynucleotides or one or more NtTS RNAi constructs.

Various embodiments are directed to expression vectors comprising one or more NtTS polynucleotides or one or more NtTS RNAi constructs encoding one or more NtTS RNAi polynucleotides capable of self-annealing to form a hairpin structure, in which the construct comprises (a) one or more NtTS polynucleotides; (b) a second sequence encoding a spacer element that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence.

The disclosed sequences can be utilized for constructing various NtTS polynucleotides that do not form hairpin structures. For example, a NtTS double-stranded RNA can be formed by (1) transcribing a first strand of the NtTS DNA by operably-linking to a first promoter, and (2) transcribing the reverse complementary sequence of the first strand of the NtTS DNA fragment by operably-linking to a second promoter. Each strand of the NtTS polynucleotide can be transcribed from the same expression vector, or from different expression vectors. The NtTS RNA duplex having RNA interference activity can be enzymatically converted to siRNAs to reduce NtTS RNA levels.

Thus, various embodiments are directed to NtTS expression vectors comprising NtTS polynucleotide or NtTS RNAi construct encoding NtTS RNAi polynucleotides capable of self-annealing, in which the construct comprises (a) one or more of the NtTS polynucleotides described herein; and (b) a second sequence comprising a complementary (for example, reverse complementary) sequence of the first sequence, positioned in the same orientation as the first sequence.

Various compositions and methods are provided for reducing the endogenous expression levels NtTS by promoting co-suppression of NtTS gene expression. The phenomenon of co-suppression occurs as a result of introducing multiple copies of a transgene into a plant cell host. Integration of multiple copies of a transgene can result in reduced expression of the transgene and the targeted endogenous gene. The degree of co-suppression is dependent on the degree of sequence identity between the transgene and the targeted endogenous gene. The silencing of both the endogenous gene and the transgene can occur by extensive methylation of the silenced loci (that is, the endogenous promoter and endogenous gene of interest) that can preclude transcription. Alternatively, in some cases, co-suppression of the endogenous gene and the transgene can occur by post transcriptional gene silencing ("PTGS"), in which transcripts can be produced but enhanced rates of degradation preclude accumulation of transcripts. The mechanism for co-suppression by PTGS is thought to resemble RNA interference, in that RNA seems to be both an important initiator and a target in these processes, and may be mediated at least in part by the same molecular machinery, possibly through RNA-guided degradation of mRNAs.

Co-suppression of NtTS nucleic acid can be achieved by integrating multiple copies of the NtTS nucleic acid or fragments thereof, as transgenes, into the genome of a plant of interest. The host plant can be transformed with an expression vector comprising a promoter operably-linked to NtTS nucleic acid or fragments thereof. Various embodiments are directed to expression vectors for promoting co-suppression of endogenous genes of NtTS comprising a promoter operably-linked to a NtTS polynucleotide.

Various embodiments are directed to methods for modulating (for example, reducing or inhibiting) the expression level of NtTS DNA by integrating multiple copies of a NtTS polynucleotide into a (tobacco) plant genome, comprising: transforming a plant cell host with an expression vector that comprises a promoter operably-linked to a NtTS polynucleotide.

Various compositions and methods are provided for reducing the endogenous gene expression level of NtTS by reducing or inhibiting the translation of NtTS mRNA. A host (tobacco) plant cell can be transformed with an expression vector comprising: a promoter operably-linked to a NtTS polynucleotide, positioned in anti-sense orientation with respect to the promoter to enable the expression of RNA polynucleotides having a sequence complementary to a portion of NtTS mRNA.

Various expression vectors for reducing or inhibiting the translation of NtTS mRNA may comprise: a promoter operably-linked to a NtTS polynucleotide in which the sequence is positioned in anti-sense orientation with respect to the promoter. The lengths of anti-sense NtTS RNA polynucleotides can vary, and may be from about 15-20 nucleotides, about 20-30 is nucleotides, about 30-50 nucleotides, about 50-75 nucleotides, about 75-100 nucleotides, about 100-150 nucleotides, about 150-200 nucleotides, and about 200-300 nucleotides.

Methods for obtaining mutant NtTS polynucleotides and polypeptides are also provided. Any plant of interest, including a plant cell or plant material can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Alternatively, NtTS genes can be targeted for inactivation by introducing ribozymes derived from a number of small circular RNAs that are capable of self-cleavage and replication in plants. These RNAs can replicate either alone (viroid RNAs) or with a helper virus (satellite RNAs). Examples of suitable RNAs include those derived from avocado sunblotch viroid and satellite RNAs derived from tobacco ringspot virus, lucerne transient streak virus, velvet tobacco mottle virus, *solanum* nodiflorum mottle virus, and subterranean clover mottle virus. Various target RNA-specific ribozymes are known to persons skilled in the art.

In some embodiments, the expression of a NtTS polypeptide is reduced by non-transgenic means, such as creating one or more mutations in a NtTS gene. Methods that introduce a mutation randomly in a gene sequence can include chemical mutagenesis, EMS mutagenesis and radiation mutagenesis. Methods that introduce one or more targeted mutations into a cell include but are not limited to genome editing technology, particularly zinc finger nuclease-mediated mutagenesis, tilling (targeting induced local lesions in genomes), homologous recombination, oligonucleotide-directed mutagenesis, and meganuclease-mediated mutagenesis.

Some non-limiting examples of mutations are deletions, insertions and missense mutations of at least one nucleotide, single nucleotide polymorphisms (SNPs) and a simple sequence repeat. After mutation, screening can be performed to identify deletions that create premature stop codons or otherwise non-functional NtTS genes. Screening of mutants can be carried out by sequencing, or by the use of one or more probes or primers specific to the NtTS gene or protein. Specific mutations in NtTS polynucleotides can also be created that can result in reduced NtTS gene expression, reduced stability of NtTS mRNA, or reduced stability of the NtTS protein. Such plants are referred to herein as mutant plants.

The mutant plants can have any combination of one or more mutations which results in reduced NtTS polypeptide levels. For example, the mutant plants may have a single mutation in a single NtTS gene or multiple mutations in a single NtTS gene. Accordingly, mutant plants comprising the mutant polypeptide variants of NtTS are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their NtTS loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the NtTS mutant plants. However, the type of plant material mutagenised may affect when the plant nucleic acid is screened for mutations. For example, when pollen is subjected to mutagenesis prior to pollination of a non-mutagenized plant, the seeds resulting from that pollination are grown into first generation plants. Every cell of the first generation plants will contain mutations created in the pollen; thus these first generation plants may then be screened for NtTS mutations instead of waiting until the second generation.

Mutagens that create point mutations, short deletions, insertions, transversions, and or transitions, including chemical mutagens or radiation, may be used to create the mutations. Mutagens include, but are not limited to, ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3-(ethyl-2-chloro-ethyl)aminopropylamino]acridine dihydrochloride (ICR-170), and formaldehyde. Spontaneous mutations in the NtTS locus that may not have been directly caused by the mutagen are also contemplated provided that they result in the desired phenotype. Suitable mutagenic agents also include, for example, ionising radiation—such as X-rays, gamma rays, fast neutron irradiation and UV radiation. Any method of plant nucleic acid preparation known to those of skill in the art may be used to prepare the plant nucleic acid for NtTS mutation screening. Any method of plant nucleic acid preparation known to those of skill in the art may be used to prepare the plant nucleic acid for NtTS mutation screening.

Prepared nucleic acid from individual plants, plant cells, or plant material can optionally be pooled in order to expedite screening for mutations in the NtTS gene of the population of plants originating from the mutagenized plant tissue, cells or material. One or more subsequent generations of plants, plant cells or plant material can be screened. The size of the optionally pooled group is dependent upon the sensitivity of the screening method used.

After the nucleic acid samples are optionally pooled, they can be subjected to NtTS polynucleotide-specific amplification techniques, such as Polymerase Chain Reaction (PCR). Any one or more primers or probes specific to the NtTS gene or the sequences immediately adjacent to the NtTS gene may be utilized to amplify the NtTS sequences within the optionally pooled nucleic acid sample. Preferably, the one or more primers are designed to amplify the regions of the NtTS locus where useful mutations are most likely to arise. Most preferably, the primer is designed to detect mutations within regions of the NtTS polynucleotide. Additionally, it is preferable for the primer(s) to avoid known polymorphic sites in order to ease screening for point mutations. To facilitate detection of amplification products, the one or more primers or probes may be labelled using any conventional labelling method. Primer(s) or probes can be designed based upon the NtTS sequences described herein using methods that are well understood in the art. Polymorphisms may be identified by means known in the art.

In a further aspect there is provided a method of preparing a mutant plant. The method involves providing at least one cell of a plant comprising a gene encoding a functional NtTS polypeptide. Next, the at least one cell of the plant is treated under conditions effective to modulate the activity of the NtTS gene. The at least one mutant plant cell is then propagated into a mutant plant, where the mutant plant has a modulated level of NtTS polypeptide as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutants plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the NtTS gene which confer a desired trait. The mutant allele(s) that occurs naturally can be transferred to the second plant by various methods including breeding, backcrossing and introgression to produce a lines, varieties or hybrids that have one or more mutations in the NtTS gene. Plants showing a desired trait may be screened out of a pool of mutant plants. Suitably, the selection is carried out utilising the knowledge of the NtTS nucleotide sequences as described herein. Consequently, it is possible to screen for a genetic trait being indicative for increased levels of free methionine as compared to a control. Such a screening approach may involve the application of conventional nucleic acid amplification and/or hybridization techniques as discussed herein. Thus, a further aspect relates to a method for identifying a mutant plant comprising the steps of: (a) providing a sample comprising a NtTS polynucleotide from a plant; and (b) determining the nucleic acid sequence of the NtTS polynucleotide, wherein a difference in the sequence of the NtTS polynucleotide as compared to the NtTS polynucleotide of a control plant is indicative that said plant is a NtTS mutant plant. In another aspect there is provided a method for identifying a mutant plant which accumulates increased levels of free methionine as compared to a control plant comprising the steps of: (a) providing a sample from a plant to be screened; (b) determining if said sample comprises one or more mutations in the NtTS polynucleotide; and (c) determining the methionine content of said plant; wherein if said sample comprises one or more mutations in the NtTS polynucleotide that modulate the expression or the activity of the protein encoded as compared to a control plant and a part of the plant has an increase in methionine content of at least 5% as compared to a control plant in which the expression or the activity of threonine synthase has not been reduced is indicative of a naturally occurring mutant plant which accumulates increased levels of free methionine. In another aspect there is provided a method for preparing a mutant plant which accumulates increased levels of free methionine as compared to a control plant comprising the steps of: (a) providing a sample from a first plant; (b) determining if said sample comprises one or more mutations in the NtTS polynucleotide that result in the accumulation of increased levels of free methionine therein; and (c) transferring the one or more mutations into a second plant. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant. In another aspect there is provided a method for preparing a mutant plant which accumulates increased levels of free methionine as compared to a control plant comprising the steps of: (a) providing a sample from a first plant; (b) determining if said sample comprises one or more mutations in the NtTS polynucleotide that result in the accumulation of increased levels of free methionine therein; and (c) introgressing the one or more mutations from the first plant into a second plant. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar. A further aspect relates to a mutant plant (including a cultivar or elite cultivar mutant plant) obtained or obtainable by the methods described herein. In certain embodiments, the mutant plants may have one or more mutations localised only to a specific region of the plant—such as within the sequence of the NtTS polynucleotide. According to this embodiment, the remaining genomic sequence of the mutant plant will be the same or substantially the same as the plant prior to the mutagenesis.

In certain embodiments, the mutant plants may have one or more mutations localised in more than one region of the plant—such as within the sequence of the NtTS polynucleotide and in one or more further regions of the genome. According to this embodiment, the remaining genomic sequence of the mutant plant will not be the same or will not be substantially the same as the plant prior to the mutagenesis. In certain embodiments, the mutant plants may not have one or more mutations in one or more, two or more, three or more, four or more or five or more exons of the NtTS polynucleotide; or may not have one or more mutations in one or more, two or more, three or more, four or more or five or more introns of the NtTS polynucleotide; or may not have one or more mutations in a promoter of the NtTS polynucleotide; or may not have one or more mutations in the 3' untranslated region of the NtTS polynucleotide; or may not have one or more mutations in the 5' untranslated region of the NtTS polynucleotide; or may not have one or more mutations in the coding region of the NtTS polynucleotide; or may not have one or more mutations in the non-coding region of the NtTS polynucleotide; or any combination of two or more, three or more, four or more, five or more; or six or more thereof parts thereof.

In one embodiment, a sequence (for example, a complementary sequence) that is at least 12, 13, 14, 15, 16, 17, 18, 19, 20, 21, 22, 23, 24, 25, 26, 27, 28, 29 or 30 or more contiguous nucleotides of nucleotides 1-46 of SEQ ID NOs: 1, 2 and 3; nucleotides 1-52 of SEQ ID NO:20; nucleotides 99-141 of SEQ ID NO:1; nucleotides 102-144 of SEQ ID NO: 2 and SEQ ID NO:3; nucleotides 102-153 of SEQ ID NO:20; nucleotides 1325-1362 of SEQ ID NOs: 1, 2 and 3; or nucleotides 1334-1371 of SEQ ID NO:20 is used to modulate expression.

In another embodiment, a sequence (for example, a complementary sequence) that is at least 12, 13, 14, 15, 16, 17, 18, 19, 20, 21, 22, 23, 24, 25, 26, 27, 28, 29 or 30 or more contiguous nucleotides of nucleotides 454-805 of SEQ ID NO:1, SEQ ID NO: 2, or SEQ ID NO:3 or nucleotides 463-814 of SEQ ID NO:20 is used to modulate expression. In a further aspect there is provided a method of identifying a plant, a plant cell or plant material comprising a mutation in a gene encoding NtTS comprising: (a) subjecting a plant, a plant cell or plant material to mutagenesis; (b) obtaining a nucleic acid sample from said plant, plant cell or plant material or descendants thereof; and (c) determining the nucleic acid sequence of the gene encoding NtTS or a variant or a fragment thereof, wherein a difference in said sequence is indicative of one or more mutations therein.

Zinc finger proteins can be used to modulate the expression or the activity of threonine synthase. In various embodiments, a genomic DNA sequence comprising a part of or all of the coding sequence of a NtTS polynucleotide is modified by zinc finger nuclease-mediated mutagenesis. The genomic DNA sequence is searched for a unique site for zinc finger protein binding. Alternatively, the genomic DNA sequence is searched for two unique sites for zinc finger protein binding wherein both sites are on opposite strands and close together, for example, 1, 2, 3, 4, 5, 6 or more basepairs apart. Accordingly, zinc finger proteins that bind to NtTS polynucleotides are provided.

A zinc finger protein may be engineered to recognize a selected target site in the NtTS gene. A zinc finger protein can comprise any combination of motifs derived from natural zinc finger DNA-binding domains and non-natural zinc finger DNA-binding domains by truncation or expansion or a process of site-directed mutagenesis coupled to a selection method such as, but not limited to, phage display selection, bacterial two-hybrid selection or bacterial one-hybrid selection. The term "non-natural zinc finger DNA-binding domain" refers to a zinc finger DNA-binding domain that binds a three-basepair sequence within the target DNA and that does not occur in the cell or organism comprising the DNA which is to be modified. Methods for the design of zinc finger protein which binds specific nucleotide sequences which are unique to a target gene are known in the art.

A zinc finger nuclease may be constructed by making a fusion of a first polynucleotide coding for a zinc finger protein that binds to a NtTS polynucleotide, and a second polynucleotide coding for a non-specific endonuclease such as, but not limited to, those of a Type IIS endonuclease. A fusion protein between a zinc finger protein and the nuclease may comprise a spacer consisting of two basepairs or alternatively, the spacer can consist of three, four, five, six, seven or more basepairs. In various embodiments, a zinc finger nuclease introduces a double stranded break in a regulatory region, a coding region, or a non-coding region of a genomic DNA sequence of a NtTS polynucleotide and leads to a reduction of the level of expression of a NtTS polynucleotide, or a reduction in the activity of the protein encoded thereby. Cleavage by zinc finger nuclease frequently results in the deletion of DNA at the cleavage site following DNA repair by non-homologous end joining.

In other embodiments, a zinc finger protein may be selected to bind to a regulatory sequence of a NtTS polynucleotide. More specifically, the regulatory sequence may comprise a transcription initiation site, a start codon, a region of an exon, a boundary of an exon-intron, a terminator, or a stop codon. Accordingly, the disclosure provides a mutant, non-naturally occurring or transgenic plant or plant cells, produced by zinc finger nuclease-mediated mutagenesis in the vicinity of or to within the NtTS gene, and methods for making such a plant or plant cell by zinc finger nuclease-mediated mutagenesis. Methods for delivering zinc finger protein and zinc finger nuclease to a plant are similar to those described below for delivery of meganuclease.

In another aspect, the disclosure further provides methods for producing mutant, non-naturally occurring or transgenic or otherwise genetically-modified plants using meganucleases—such as I-Crel. Naturally occurring meganucleases as well as recombinant meganucleases can be used to specifically cause a double-stranded break at a single site or at relatively few sites in the genomic DNA of a plant to allow for the disruption of a NtTS gene. The meganuclease may be an engineered meganuclease with altered DNA-recognition properties. Meganuclease proteins can be delivered into plant cells by a variety of different mechanisms known in the art.

The disclosure encompasses the use of meganucleases to inactivate NtTS polynucleotides in a plant cell or plant. Particularly, the disclosure provides a method for inactivating a NtTS polynucleotide in a plant using a meganuclease comprising: (a) providing a plant cell comprising a NtTS polynucleotide; (b) introducing a meganuclease or a construct encoding a meganuclease into said plant cell; and (c) allowing the meganuclease to substantially inactivate the NtTS polynucleotide.

Meganucleases can be used to cleave meganuclease recognition sites within the coding regions of a NtTS polynucleotide. Such cleavage frequently results in the deletion of DNA at the meganuclease recognition site following mutagenic DNA repair by non-homologous end joining. Such mutations in the gene coding sequence are typically sufficient to inactivate the gene. This method to modify a plant cell involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques. Alternatively, plant cells may be initially be transformed with a meganuclease expression cassette lacking a selectable marker and may be grown on media lacking a selection agent. Under such conditions, a fraction of the treated cells will acquire the meganuclease expression cassette and will express the engineered meganuclease transiently without integrating the meganuclease expression cassette into the genome. Because it does not account for transformation efficiency, this latter transformation procedure requires that a greater number of treated cells be screened to obtain the desired genome modification. The above approach can also be applied to modify a plant cell when using a zinc finger protein or zinc finger nuclease.

Following delivery of the meganuclease expression cassette, plant cells are grown, initially, under conditions that are typical for the particular transformation procedure that was used. This may mean growing transformed cells on media at temperatures below 26° C., frequently in the dark. Such standard conditions can be used for a period of time, preferably 1-4 days, to allow the plant cell to recover from the transformation process. At any point following this initial recovery period, growth temperature may be raised to stimulate the activity of the engineered meganuclease to cleave and mutate the meganuclease recognition site.

For certain applications, it may be desirable to precisely remove the NtTS polynucleotide from the genome of the plant. Such applications are possible using a pair of engineered meganucleases, each of which cleaves a meganuclease recognition site on either side of the intended deletion.

Plants suitable for use in genetic modification according to the disclosure include monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species may include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), *Triticosecale* (triticum—wheatxrye), bamboo, *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Brassica juncea, Beta vulgaris* (sugarbeet), *Manihot esculenta* (cassava), *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Rosa* spp. (rose), *Dianthus caryophyllus* (carnation), *Petunia* spp. (petunia), *Poinsettia pulcherrima* (poinsettia), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy), *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Various embodiments are directed to mutant plants, non-naturally occurring plants or transgenic plants modified to reduce NtTS gene expression levels thereby, producing plants—such as tobacco plants—in which the expression level of NtTS is reduced within plant tissues of interest as compared to a control plant. The disclosed compositions and methods can be applied to any species of the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis, N. acuminata, N. acuminata* var. *multiflora, N. africana, N. alata, N. amplexicaulis, N. arentsii, N. attenuata, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata,*

*N. rosulata* subsp. *ingulba*, *N. rotundifolia*, *N. setchellii*, *N. simulans*, *N. solanifolia*, *N. spegazzinii*, *N. stocktonii*, *N. suaveolens*, *N. sylvestris*, *N. thyrsiflora*, *N. tomentosa*, *N. tomentosiformis*, *N. trigonophylla*, *N. umbratica*, *N. undulata*, *N. velutina*, *N. wigandioides*, and *N. x sanderae*.

The transgenic, non-naturally occurring or mutant plant may therefore be a tobacco variety or elite tobacco cultivar that comprises one or more transgenes, or one or more genetic mutations or a combiantion thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar). Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVH03, PVH09, PVH19, PVHSO, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B 13P, Xanthi (Mitchell-Mor), Bel-W3, 79-615, Samsun Holmes N N, KTRDC number 2 Hybrid 49, Burley 21, KY 8959, KY 9, MD 609, PG 01, PG 04, PO1, PO2, PO3, RG 11, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HBO4P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

Embodiments are also directed to compositions and methods for producing mutant plants, non-naturally occurring plants, hybrid plants, or transgenic plants that have been modified to reduce threonine synthase expression or activity which results in an increase in the free methionine concentration in one or more parts (for example, the leaves) of a plant as compared to a control. Advantageously, the mutant plants, non-naturally occurring plants, hybrid plants, or transgenic plants that are obtained are similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect is a seed of a mutant plant, a non-naturally occurring plant, a hybrid plant, a transgenic plant of the disclosure. Preferably, the seed is a tobacco seed. A further aspect of the disclosure is pollen or an ovule of a mutant plant, a non-naturally occurring plant, a hybrid plant, a transgenic plant of the disclosure. In addition, there is provided a mutant plant, a non-naturally occurring plant, a hybrid plant, a transgenic plant as described which further comprises a nucleic acid conferring male sterility.

The disclosure also provides a tissue culture of regenerable cells of the mutant plant, non-naturally occurring plant, hybrid plant, or transgenic plant or a part thereof which culture regenerates plants capable of expressing all the morphological and physiological characteristics of the parent. The regenerable cells of the disclosure include but are not limited to cells from leaves, pollen, embryos, cotyledons, hypocotyls, roots, root tips, anthers, flowers and a part thereof, ovules, shoots, stems, stalks, pith and capsules or callus or protoplasts derived therefrom.

In one embodiment, the stalk height of the mutant, non-naturally occurring or transgenic plants is substantially the same as the control plants at three months after field transplant or 36 days after topping. For example, the stalk height of the mutant, non-naturally occurring or transgenic plants is not less than the stalk height of the control plants three months after field transplant or 36 days after topping. In another embodiment, the stalk height of the mutant, non-naturally occurring or transgenic plants is about 10%, 9%, 8%, 7%, 6%, 5%, 4%, 3%, 2% or 1% higher or lower than the control plants at three months after field transplant or 36 days after topping. In another embodiment, the chlorophyll content of the mutant, non-naturally occurring or transgenic plants is substantially the same as the control plants at three months after field transplant or 36 days after topping. For example, the chlorophyll content of the mutant, non-naturally occurring or transgenic plants is not less than the chlorophyll content of the control plants three months after field transplant or 36 days after topping. In another embodiment, the chlorophyll content of the mutant, non-naturally occurring or transgenic plants is about 10%, 9%, 8%, 7%, 6%, 5%, 4%, 3%, 2% or 1% higher or lower than the control plants at three months after field transplant or 36 days after topping. In another embodiment, the stalk height of the mutant, non-naturally occurring or transgenic plants is substantially the same as the control plants at three months after field transplant or 36 days after topping and the chlorophyll content of the mutant, non-naturally occurring or transgenic plants is substantially the same as the control plants at three months after field transplant or 36 days after topping. For example, the stalk height of the mutant; non-naturally occurring or transgenic plants is not less than the stalk height of the control plants three months after field transplant or 36 days after topping and the chlorophyll content of the mutant, non-naturally occurring or transgenic plants is not less than the chlorophyll content of the control plants three months after field transplant or 36 days after topping. In another embodiment, the stalk height of the mutant, non-naturally occurring or transgenic plants is about 10%, 9%, 8%, 7%, 6%, 5%, 4%, 3%, 2% or 1% higher or lower than the control plants at three months after field transplant or 36 days after topping and the chlorophyll content of the mutant, non-naturally occurring or transgenic plants is about 10%, 9%, 8%, 7%, 6%, 5%, 4%, 3%, 2% or 1% higher or lower than the control plants at three months after field transplant or 36 days after topping. In other embodiments, any one or more of the following characteristics: degree of maturity, number of leaves per plant, stalk height, leaf insertion angle, leaf size (width and length), internode distance, lamina-midrib ratio, and colouration of the leaves of the mutant, non-naturally occurring or transgenic plants is substantially the same as the control plants at three months after field transplant or 36 days after topping.

In another aspect, there is provided a method for increasing the concentration of free methionine in at least a part of a plant (for example, the leaves), comprising the steps of: (i) reducing the expression or activity of threonine synthase in the plant, preferably, wherein the threonine synthase comprises the polynucleotide sequence described herein or the polypeptide sequence described herein; (ii) measuring the concentration of free methionine in at least a part (for example, the leaves) of the mutant, non-naturally occurring plant or transgenic plant obtained in step (i); and (iii) identifying a mutant, non-naturally occurring or transgenic plant in which the concentration of free methionine therein has increased in comparison. to a control plant. Suitably, the overall appearance of said mutant, non-naturally occurring or transgenic plant is substantially the same as the control plant three months after field transplant or 36 days after topping. Suitably, the free threonine concentration in part of the plant—such as the leaves —is increased as compared to the control plant.

The reduction in expression of threonine synthase as compared to the control plant may be from about 5% to about 100%, from about 5% to about 99% or less, from about 5% to about 95% or less, from about 5% to about 90% or less, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional activity and/or protein expression. In one embodiment, the reduction in expression of threonine synthase is a partial reduction in expression, which includes a reduction in transcriptional activity and/or protein expression. In one embodiment, the partial reduction in expression allows the mutant, non-naturally occurring or transgenic plant or plant cell to maintain residual levels of threonine synthase.

The reduction in the activity of threonine synthase as compared to a control plant may be from about 5% to about 100%, from about 5% to about 99% or less, from about 5% to about 95% or less, from about 5% to about 90% or less, or a reduction of at least 10%, at least 20%, at least 25%, at least 30%, at least 40%, at least 50%, at least 60%, at least 70%, at least 75%, at least 80%, at least 90%, at least 95%, at least 98%, or 100% or more. In one embodiment, the reduction in activity of threonine synthase is a partial reduction in activity. In one embodiment, the partial reduction in activity allows the mutant, non-naturally occurring or transgenic plant or plant cell to maintain residual levels of threonine synthase.

The increase in the free threonine concentration as compared to a control plant may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or up to 100%.

In certain embodiments, the expression of SEQ ID NO:1 or SEQ ID NO:2 or SEQ ID NO:3 or SEQ ID NO:20 or the activity of the protein encoded thereby is reduced (for example, silenced or inhibited). In certain embodiments, the expression of SEQ ID NO:1 and SEQ ID NO:2 or SEQ ID NO:3 or SEQ ID NO:20 or the activity of the protein encoded thereby is reduced (for example, silenced or inhibited). In certain embodiments, the expression of SEQ ID NO:1 or SEQ ID NO:2 and SEQ ID NO:3 or SEQ ID NO:20 or the activity of the protein encoded thereby is reduced (for example, silenced or inhibited). In certain embodiments, the expression of SEQ ID NO:1 or SEQ ID NO:2 or SEQ ID NO:3 and SEQ ID NO:20 or the activity of the protein encoded thereby is reduced (for example, silenced or inhibitied). In certain embodiments, the expression of SEQ ID NO:1, SEQ ID NO:2, SEQ ID NO:3 and SEQ ID NO:20 or the activity of the protein encoded thereby is reduced (for example, silenced or inhibitied). In certain embodiments, the expression of SEQ ID NO:2, SEQ ID NO:3 and SEQ ID NO:20 or the activity of the protein encoded thereby is reduced (for example, silenced or inhibited). In certain embodiments, the expression of SEQ ID NO:2, SEQ ID NO:3 and SEQ ID NO:20 or the activity of the protein encoded thereby is reduced (for example, silenced or inhibitied). In certain embodiments, the expression of SEQ ID NO:1, SEQ ID NO:3 and SEQ ID NO:20 or the activity of the protein encoded thereby is reduced (for example, silenced or inhibited). In certain embodiments, the expression of SEQ ID NO:1, SEQ ID NO:2 and SEQ ID NO:20 or the activity of the protein encoded thereby is reduced (for example, silenced or inhibitied). In certain embodiments, the expression of SEQ ID NO:1, SEQ ID NO:2 and SEQ ID NO:3 or the activity of the protein encoded thereby is reduced (for example, silenced or inhibited). In certain embodiments, the expression of each of SEQ ID NO:1, SEQ ID NO:2, or SEQ ID NO: 3, or the activity of each of the proteins encoded thereby, individually or in a combination, is reduced to a greater extent than the expression of SEQ ID NO:20. In one embodiment, the addition of exogenous ingredients—such as amino acids—for example, threonine and/or isoleucine—is not required in order to obtain plants of acceptable visual appearance.

One object is to provide mutant plants, transgenic plants or non-naturally occurring plants that exhibit an increased level of free methionine while maintaining substantially the same visual appearance and one or more agronomic characteristics as compared to a control plant. Accordingly, there is described herein mutant plants, transgenic plants or non-naturally occurring plants or genetically modified cells that have an increased level of free methionine and a reduced threonine synthase activity or expression as compared to control tobacco cells or control plants. The mutant, transgenic or non-naturally occurring plants or cells have been modified to reduce the synthesis of threonine synthase by reducing the expression of one or more polypeptides encoding the polynucleotide sequences described herein, preferably encoded by one or more polynucleotides comprising, consisting or consisting essentially of a sequence encoding a threonine synthase and having at least 87%, 88%, 89%, 90%, 95%, 96%, 97%, 98%, 99% and 100% sequence identity to SEQ ID NO:1, SEQ ID NO:2 and/or SEQ ID NO:3 or by one or more polynucleotides comprising, consisting or consisting essentially of a sequence encoding a threonine synthase and having at least 90%, 91%, 92%, 93%, 94%, 95%, 96%, 97%, 98% or 100% sequence identity to sequence SEQ ID NO:4, SEQ ID NO:5, SEQ ID NO:6 or SEQ ID NO:20.

A further aspect, relates to mutant plants, non-naturally occurring plants or transgenic plants, wherein expression of threonine synthase or the activity of the protein encoded thereby is reduced and a part of the plant (for example, the leaves) has an increase in methionine content of at least 5% as compared to a control plant in which the expression or the activity of threonine synthase has not been reduced. Preferably, the methional concentration in the smoke or aerosol of tobacco products is increased by at least 5% as compared to the smoke or aerosol of tobacco product made from the control plant.

The increase in the methionine content as compared to the control plant may be at least about 5%, at least about 10%, at least about 20%, at least about 25%, at least about 30%, at least about 40%, at least about 50%, at least about 60%, at least about 70%, at least about 75%, at least about 80%, at least about 90%, at least about 95%, at least about 96%, at least about 97%, at least about 98%, at least about 99%, or about 100% or more.

The increase in the methional concentration in the smoke or aerosol prepared from tobacco product as compared to the control plant may be at least about 5%, at least about 10%, at least about 20%, at least about 25%, at least about 30%, at least about 40%, at least about 50%, at least about 60%, at least about 70%, at least about 75%, at least about 80%, at least about 90%, at least about 95%, at least about 96%, at least about 97%, at least about 98%, at least about 99%, or about 100% or more.

Suitably, the visual appearance or one or more agronomic characteristics of said plant is substantially the same as the control plant three months after field transplant or 36 days after topping, preferably, wherein the stalk height of the mutant, non-naturally occurring or transgenic plants is substantially the same as the stalk height of the control plants three months after field transplant or 36 days after topping and/or the chlorophyll content of the mutant, non-naturally occurring or transgenic plants is substantially the same as the chlorophyll content of the control plants three months after field transplant or 36 days after topping.

Suitably, the free methionine concentration in a part of the plant (for example, the leaves) is increased as compared to the control plant.

Suitably, (i) the free methionine concentration in part of the plant (for example, the leaves) is at least about 0.026 mg/g, suitably at least about 0.027 mg/g, suitably at least about 0.028 mg/g, suitably at least about 0.029 mg/g, suitably at least about 0.03 mg/g, suitably at least about 0.031 mg/g, suitably at least about 0.032 mg/g, suitably at least about 0.032 mg/g, suitably at least about 0.033 mg/g, suitably at least about 0.034 mg/g; (ii) the free threonine concentration in part of the plant (for example, the leaves) is at least about 0.5 mg/g, suitably at least about 0.52 mg/g, suitably at least about 0.54 mg/g, suitably at least about 0.56 mg/g, suitably at least about 0.58 mg/g, suitably at least about 0.6 mg/g; and (iii) the methional concentration in aerosol upon heating part of the plant (for example, the leaves) is at least about 2000 µg/g, suitably at least about 2100 µg/g, suitably at least about 2200 µg/g, suitably at least about 2500 µg/g, suitably at least about 2750 µg/g, suitably at least about 3000 µg/g, suitably at least about 3250 µ/g, suitably at least about 3500 µg/g, suitably at least about 3750 µg/g, suitably at least about 3800 µg/g or higher.

Suitably, (i) the free methionine concentration in part of the plant (for example, the leaves) is at least about 0.03 mg/g; (ii) the free threonine concentration in part of the plant (for example, the leaves) is between about 0.5 mg/g to 0.65 mg/g; and (iii) the methional concentration in aerosol upon heating part of the plant (for example, the leaves) is at least about 2200 µg/g.

Suitably, (i) the free methionine concentration in part of the plant (for example, the leaves) is at least about 0.03 mg/g; (ii) the free threonine concentration in part of the plant (for example, the leaves) is between about 0.5 mg/g to 0.65 mg/g; and (iii) the methional concentration in aerosol upon heating part of the plant (for example, the leaves) is between about 2200 µg/g and about 4000 µg/g, suitably between about 2200 µg/g and about 3850 µg/g.

The plant may be heated to 100° C. or above—such as at least 125° C., at least 150° C., at least 175° C. or at least 200° C.—to release the aerosol.

In a still further aspect, there is provided a mutant plant, a non-naturally occurring plant, or a transgenic plant, wherein expression of threonine synthase or the activity of the protein encoded thereby is reduced and (i) the free methionine concentration in part of the plant (for example, the leaves) is about 0.03 mg/g; (ii) the free threonine concentration in part of the plant (for example, the leaves) is about 0.5 to about 0.7 mg/g; and (iii) the methional concentration in aerosol upon heating part of the plant (for example, the leaves) is at least about 2000 µg/g, and suitably wherein the visual appearance or one or more agronomic characteristics of said plant is substantially the same as the control plant three months after field transplant or 36 days after topping, preferably, wherein the stalk height of the mutant, non-naturally occurring or transgenic plants is substantially the same as the stalk height of the control plants three months after field transplant or 36 days after topping and/or the chlorophyll content of the mutant, non-naturally occurring or transgenic plants is substantially the same as the chlorophyll content of the control plants three months after field transplant or 36 days after topping.

According to the disclosure, a plant carrying a modified threonine synthase allele can be used in a plant breeding program to create useful lines, varieties and hybrids. A modified allele can be a mutant allele. In particular, the modified threonine synthase allele is introgressed into the commercially important varieties as described above. Thus, methods for breeding plants are provided, that comprise crossing a mutant plant, a non-naturally occurring plant or a transgenic plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the disclosure.

In one embodiment, a method is provided for producing a non-naturally occurring plant comprising: (a) crossing a mutant or transgenic plant with a second plant to yield progeny tobacco seed; (b) growing the progeny tobacco seed, under plant growth conditions, to yield the non-naturally occurring plant. The method may further comprises: (c) crossing the previous generation of non-naturally occurring plant with itself or another plant to yield progeny tobacco seed; (d) growing the progeny tobacco seed of step (c) under plant growth conditions, to yield additional non-naturally occurring plants; and (e) repeating the crossing and growing steps of (c) and (d) multiple times to generate further generations of non-naturally occurring plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly tobacco plant breeding, are well known and can be used in the methods of the disclosure. The disclosure further provides non-naturally occurring plants produced by these methods.

In some embodiments of methods described herein, lines resulting from breeding and screening for variant threonine synthase genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical, and other common testing before and during curing. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed modified or mutant alleles of the threonine synthase gene into other tobaccos, as described herein. For example, a breeder can create segregating populations from hybridizations of a genotype containing a mutant allele with an agronomically desirable genotype. Plants in the F2 or backcross generations can be screened using a marker developed from a threonine synthase genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

According to the disclosure, in a breeding program, successful crosses yield F1 plants that are fertile. Selected F1 plants can be crossed with one of the parents, and the first backcross generation plants are self-pollinated to produce a population that is again screened for variant threonine synthase gene expression (for example, the null version of the threonine synthase gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant threonine synthase gene expression. In some embodiments, a plant population in the F2 generation is screened for variant threonine synthase gene expression, for example, a plant is identified that fails to express threonine synthase due to the absence of a threonine synthase gene according to standard methods, for example, by using a PCR method with primers based upon the nucleotide sequence information for threonine synthase described herein.

Hybrid varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression of NtTS polypeptide or polynucleotide. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides or polynucleotides.

Mutant, non-naturally occurring or transgenic plant cells and plants are described herein comprising one or more recombinant polynucleotides—such as one or more isolated NtTS polynucleotides, one or more polynucleotide constructs, one or more double-stranded RNAs, one or more conjugates or one or more vectors/expression vectors.

In some embodiments, a plant in which expression of a NtTS polynucleotide is reduced can have an increase in the free methionine concentration, especially in the leaves. The free methionine concentration can be increased by at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 70%, 80%, 90%, 95%, 96%, 97%, 98%, 99% or 100% or more as compared to the free methionine concentration in a corresponding control plant in which expression of NtTS polynucleotide has not been reduced.

In some embodiments, a plant in which expression of a NtTS polynucleotide is reduced can have a decrease in the free threonine concentration, especially in the leaves. The free threonine concentration can be decreased by at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 70%, 80%, 90%, 95%, 96%, 97%, 98%, 99% or 100% or more as compared to the free threonine concentration in a corresponding control plant in which expression of NtTS polynucleotide has not been reduced. In one embodiment, the free threonine concentration can be decreased by at least about 20%, 25%, 30%, 35%, 40%, 45%, 50%, 55%, 60%, 70%, or 80% or more as compared to the free threonine concentration in a corresponding control plant in which expression of NtTS polynucleotide has not been reduced.

Expression of NtTS can be evaluated using methods including, for example, RT-PCR, Northern blots, RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, for example, at a particular time in development or upon induction, expression can be evaluated selectively at a desired time period.

Without limitation, the plants described herein may be modified for other purposes either before or after the expression or activity of threonine synthase has been modulated. One or more of the following additional genetic modifications can be present in the mutant, non-naturally occurring or transgenic plants of the disclosure. In one embodiment, one or more genes that are involved in heavy metal uptake or heavy metal transport is modified resulting in plants or parts of plants (such as leaves) having a lower heavy metal content than control plants or parts thereof without the modification(s). Non-limiting examples include genes belonging to the family of cation diffusion facilitators (CDF), the family of Zrt-, Ift-like proteins (ZIP), the family of cation exchangers (CAX), the family of copper transporters (COPT), the family of heavy-metal P-type ATPases (HMAs, as described in WO2009074325), the family of homologs of natural resistance-associated macrophage proteins (NRAMP), and the family of ATP-binding cassette (ABC) transporters, which participate in transport of heavy metals. The term heavy metal as used herein includes transition metals. In another embodiment, one or more genes that are involved in the conversion of nitrogenous metabolic intermediates is modified resulting in plants or parts of plants (such as leaves) that when heated, produces lower levels of at least one tobacco-specific nitrosamine (for example, 4-(methylnitrosamino)-1-(3-pyridyl)-1-butanone, N-nitrosonornicotine, N-nitrosoanatabine, and N-nitrosoanabasine) than control plants or parts thereof. Non-limiting examples of genes that can be modified include genes encoding a nicotine demethylase; such as CYP82E4, CYP82E5 and CYP82E10 which participate in the conversion of nicotine to nornicotine and are described in WO2006091194, WO2008070274, WO2009064771 and PCT/US2011/021088.

Examples of other modifications include herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. OB protein of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*. Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single protein and significantly delayed the evolution of resistant insects. Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered. Another exemplary modification results in altered reproductive capability, such as male sterility. Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance. Another exemplary modification results in plants that produce proteins which have favourable immunogenic properties for use in humans. For example, plants capable of producing proteins which substantially lack alpha-1,3-linked fucose residues, beta-1,2-linked xylose residues, or both, in its N-glycan may be of use. Other exemplary modifications can result in plants with improved storage proteins and oils, plants with enhanced photosynthetic efficiency, plants with prolonged shelf life, plants with enhanced carbohydrate content, and plants resistant to fungi; plants encoding an enzyme involved in the biosynthesis of alkaloids. Transgenic plants in which the expression of S-adenosyl-L-methionine (SAM) and/or cystathionine gamma-synthase (CGS) has been modulated are also contemplated.

One or more such traits may be introgressed into the mutant, non-naturally occurring or transgenic tobacco plants of the disclosure from another tobacco cultivar or may be directly transformed into it. The introgression of the trait(s) into the mutant, non-naturally occurring or transgenic plants of the disclosure maybe achieved by any method of plant breeding known in the art, for example, pedigree breeding, backcrossing, doubled-haploid breeding, and the like (see, Wernsman, E. A, and Rufty, R. C. 1987. Chapter Seventeen. Tobacco. Pages 669-698 In: *Cultivar Development. Crop Species*. W. H. Fehr (ed.), MacMillan Publishing Co, Inc., New York, N.Y. 761 pp.). Molecular biology-based techniques described above, in particular RFLP and microsatelite markers, can be used in such backcrosses to identify the progenies having the highest degree of genetic identity with the recurrent parent. This permits one to accelerate the production of varieties having at least 90%, preferably at least 95%, more preferably at least 99% genetic identity with the recurrent parent, yet more preferably genetically identical to the recurrent parent, and further comprising the trait(s) introgressed from the donor parent. Such determination of genetic identity can be based on molecular markers known in the art.

The last backcross generation can be selfed to give pure breeding progeny for the nucleic acid(s) being transferred. The resulting plants generally have essentially all of the morphological and physiological characteristics of the mutant, non-naturally occurring or transgenic plants of the disclosure, in addition to the transferred trait(s) (for example, one or more single gene traits). The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred.

Various embodiments provide mutant plants, non-naturally occurring plants or transgenic plants, as well as biomass in which the expression level of NtTS polynucleotide is reduced to increase the free methionine concentration therein—particularly in but not limited to the leaves.

Parts of the such plants, particularly tobacco plants, and more particularly the leaf lamina and midrib of tobacco plants, can be incorporated into or used in making various consumable products including but not limited to aerosol forming materials, aerosol forming devices, smoking articles, smokable articles, smokeless products, and tobacco products. Examples of aerosol forming materials, particularly nicotine aerosol-forming materials include but are not limited to tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices, including nicotine aerosol-forming devices. Examples of smoking articles or smokable articles include but are not limited to cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around, adjacent to or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes (for example, cigarette smoke), or by combusting an aerosol forming material.

In one embodiment, there is also provided cured plant material including cured leaves or cured plant parts from the mutant, transgenic and non-naturally occurring tobacco plants described herein. Processes of curing green tobacco leaves are known by those having skills in the art and include without limitation air-curing, fire-curing, flue-curing and sun-curing. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured.

In another embodiment, there is described tobacco products including nicotine aerosol-forming materials or tobacco-containing aerosol forming materials comprising leaves, preferably cured leaves, made from leaves of mutant tobacco plants, transgenic tobacco plants or non-naturally occurring tobacco plants described herein. The tobacco products described herein can be a blended tobacco product which may further comprise tobacco from one or more other varieties of tobacco plants, including unmodified tobacco plants.

The percentage free methionine in the aerosol forming materials or tobacco compositions of the disclosure is a value of at least about 5%, 10%, 15%, 20%, 25%, 30%, 35%, 40%, 45%, t, 55%, 60%, 65%, 70%, 75%, 80%, 85%, 90%, 95%, 96%, 97%, 98%, 99%, and 100% higher, when compared to aerosol forming materials or tobacco compositions derived from non-mutant, non-naturally occurring or non-transgenic counterpart plants.

The mutant, non-naturally occurring or transgenic plants may have other uses in, for example, agriculture. For example, mutant, non-naturally occurring or transgenic plants described herein can be used to make animal feed and human food products.

The disclosure also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the packaging material, or a label inserted within the package that describes the nature of the seeds therein.

A further aspect relates to a method for producing methional comprising the steps of: (a) providing part of a mutant, non-naturally occurring or transgenic plant; biomass, seed or leaves; or the aerosol forming materials as described herein; and (b) providing heat thereto.

Compositions, methods and kits for genotyping plants for identification, selection, or breeding are encompassed by the disclosure and can comprise a means of detecting the presence of a NtTS polynucleotide in a sample of polynucleotide. Accordingly, a composition is described comprising one of more primers for specifically amplifying at least a portion of NtTS polynucleotide and optionally one or more probes and optionally one or more reagents for conducting the amplification or detection. Accordingly, gene specific oligonucleotide primers or probes comprising about 10 or more contiguous polynucleotides corresponding to the NtTS polynucleotide are dislcosed. Said primers or probes may comprise or consist of about 15, 20, 25, 30, 40, 45 or 50 more contiguous polynucleotides that hybridise (for example, specifically hybridise) to the NtTS polynucleotide. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in nucleic acid amplification or detection). The one or more specific primers or probes can be designed and used to amplify or detect a part or all of the NtTS polynucleotide. By way of specific example, two primers may be used in a polymerase chain reaction protocol to amplify a nucleic acid fragment encoding NtTS nucleic acid—such as DNA or RNA. The polymerase chain reaction may also be performed using one primer that is derived from the NtTS nucleic acid sequence and a second primer that hybridises to a sequence upstream or downstream of the NtTS nucleic acid sequence—such as a NtTS promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

Thus, in a further aspect, there is also provided a method of detecting a NtTS polynucleotide in a sample comprising the step of: (a) providing a sample comprising, or suspected of comprising, a polynucleotide; (b) contacting said sample with one of more primers or one or more probes for specifically detecting at least a portion of NtTS polynucleotide; and (c) detecting the presence of an amplification product, wherein the presence of an amplification product is indicative of the presence of the NtTS polynucleotide in the sample. In a further aspect, there is also provided the use of one of more primers or probes for specifically detecting at least a portion of the NtTS polynucleotide. Kits for detecting at least a portion of the NtTS polynucleotide are also provided which comprise one of more primers or probes for specifically detecting at least a portion of NtTS polynucleotide. The kit may comprise reagents for polynucleotide amplification—such as polymerase chain reaction (PCR)—or reagents for nucleic acid probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and/or instructions for determining methionine, threonine and/or methional content. In some embodiments, a kit may comprise instructions for one or more of the methods described. The kits described may be useful for genetic identity determination, phylogenetic studies, genotyping, haplotyping, pedigree analysis or plant breeding particularly with co-dominant scoring.

The present disclosure also provides a method of genotyping a plant, a plant cell or plant material comprising a NtTS polynucleotide. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by nucleotide sequence variability. Thus, the present disclosure further provides a means to follow segregation of a NtTS gene or nucleic acid as well as chromosomal sequences genetically linked to these genes or nucleic acids using such techniques as AFLP analysis.

The correlation between methionine produced in plants resulting from threonine synthase silencing, and chemical compounds found in cured tobacco have been monitored in cured leaves using mass spectrometry. The mass spectrometry profiles of plant extracts indicate that silencing threonine synthase in plants carries forward changes in the plants since four peaks showed altered profiles in threonine synthase silenced-lines as compared to extracts from control plants (see FIG. 1). Three peaks increase in abundance, whereas one reduces in abundance. These changes in profile can be used to identify plants in which the levels of methional in aerosol is likely to be increased. Accordingly, in a further aspect, there is provided a method for identifying tobacco material that releases elevated levels of methional into an aerosol upon heating, comprising the steps of: (a) preparing a sample of tobacco material; (b) determining the molecular mass profile of the sample; and (c) comparing the molecular mass profile at one or more of a mass:charge ratio to that of a control plant; wherein a specific change in the mass:charge ratio as compared to a control plant is indicative that the levels of methional in the aerosol is elevated. Suitably, the molecular mass is measured by mass spectrometry, preferably, liquid chromatography-mass spectrometry (LC-MS), gas chromatography-mass spectrometry (GC-MS). In a further aspect, there is provided tobacco material identified or identifiable by this method.

The disclosure is further described in the Examples below, which are provided to describe the invention in further detail. These examples, which set forth a preferred mode presently contemplated for carrying out the invention, are intended to illustrate and not to limit the invention.

EXAMPLES

Example 1

Identification of Tobacco Threonine Synthase

The tobacco threonine synthase gene is identified using tobacco EST sequences found in the Tobacco Genome Initiative. Another tobacco EST contig (NCBI_45312-v2pep-fl) close to tobacco threonine synthase is assembled from the NCBI EST sequences. This coding sequence has exactly the same length (1569 bp) as the tobacco threonine synthase. Data using DNA-microarray exon Affymetrix chips (sequence probes from NtPMIa1g193542e1) shows that tobacco threonine synthase is equally expressed in roots, trichomes, green and senescent leaves of *N. tabacum*. No major changes in gene expression levels were found between leaf of Flue-cured (K326, K399) and Burley (TN90, Bu64) tobacco. In addition, cold and cadmium stress does not affect tobacco threonine synthase expression levels, thereby indicating that this threonine synthase is very likely constitutively expressed in tobacco leaf

Example 2

Overexpression of Cystathionine Gamma-Synthase (CGS)

*Arabidopsis thaliana* CGS (MT01, TAIR Accession AT3901120) is introduced under transcriptional control of the cauliflower mosaic virus 35S promoter into Burley tobacco TN90 via *Agrobacterium tumefasciens* using a classical leaf disk procedure as described in the literature. The kanamycin antibiotic selection gene is also inserted.

Example 3

Silencing of Threonine Synthase Expression in Tobacco Plants

Using a DNA fragment of SEQ ID NO:1, primers are generated to silence NtTS in tobacco using a RNAi approach. The primers used are 5'-ctgaaatcgacagcgatgata-3' (SEQ ID NO: 9) and 5'-caaccaatagctaacggagctt-3' (SEQ ID NO: 10). The corresponding RNAi sequence is amplified from cDNA by reverse transcriptase-polymerase chain reaction (RT-PCR) and then inserted into the Gateway vector pB7GWIWG2(II) via an entry vector, exactly as detailed by the manufacturer (Invitrogen). This vector contains a promoter for constitutive expression (the cauliflower mosaic virus CaMV 35S promoter) of the transgene in all tissues of the plant and the kanamycin gene for kanamycin antibiotic selection on agar plates (100 mg/ml). The construct is then inserted into the genome of the Burley tobacco TN90 via *Agrobacterium tumefasciens* using a classical leaf disk procedure. From calli, individual lines are regenerated and selected on kanamycin. RNAi silencing T0 lines are monitored by (i) RT-PCR and grown for seed production on genomic DNA using one primer in the 35S promoter (5'-gagcatcgtggaaaaagaagac-3') and one primer within the fragment used for silencing (5'-aagctccgttagctattggttg-3') and by (ii) RT-PCR using specific primers flanking the insert used for silencing (5'-ttgattcacgtgtcggtaagac-3') and grown for seed production. T1 seeds are collected, re-grown on kanamycin-containing agar and monitored exactly as T0 plantlets. PCR on genomic gDNA shows that the NtTS DNA fragment is inserted into the genome and effectively silences tobacco threonine synthase.

Example 4

Cultivation of Threonine Synthase Silenced Tobacco Plants

Kanamycin resistant plants are grown in floating trays before cultivation in the field (Kentucky, US). Twenty plants of the silenced threonine synthase line (NtTS-RNAi line; Example 2), cystathionine gamma-synthase line (Example 3), a vector control (VC, pB7GWIWG2(II)) and a TN90 US background tobacco are cultivated in four replicates of 20 plants. Three months after field transplant (36 days after topping), one leaf in mid-stalk position is sampled in 10 identical. plants out of the 20 for each replicate. The leaves ("green leaves") are immediately stored in dry ice and lyophilized. Ten plants from the best two lines are selected and then cured according to Burley agricultural practices. After curing, three leaves at mid-stalk position are sampled. To monitor the silencing effect in the silenced threonine synthase lines and to compare with the cystathionine gamma-synthase lines, "green leaves" from three lines are ground and subjected to free amino acid analyses.

Example 5

Methional Analysis

The correlation between methionine produced in green leaves, resulting from threonine synthase silencing, and chemical compounds found in cured tobacco are monitored in cured leaves using LC-MS using the lines described above. The extraction is performed in methanol. The equipment used is a Waters Acquity UPLC system coupled to MS. The column is a WatersXBridge Shield RP18 using as mobile phase A water:acetonitrile (95:5 v/v) and as mobile phase B methanol. The LC-MS profiles indicate that silencing threonine synthase in green leaves carries forward a chemical signal in cured leaves. Indeed four peaks showed altered profiles in threonine synthase silenced-lines compared to controls (see FIG. 1). Three peaks clearly increase in abundance, whereas one reduces. This suggests that methionine that accumulates in green leaves is converted either to degradation sulfur products or methionine derivatives in cured leaves.

As methionine is a possible precursor of methional, we analyzed the content of methional in the aerosol formed after heating cured tobacco (TN90, VC, NtTS-1, NtTS-1 and NtTS-3 selected filed replicates) and subject to cold trap. The smoking platform used is a smoke-simulator with a Macor type heat source (54W) including a regime of 12 Puff of 2s. Before smoking, tobacco cured lamina was cut and impregnated with 20% glycerin. The aerosols produced by heating impregnated cured tobaccos (100 mg, 3 full replicates) were condensed using a cryogenic system developed by Air Liquid and dissolved in dichloromethane (2 times 5 mL). The methional levels in aerosol solutions were determined by GC-MS after derivatization. Ion producing the most abundant signal was used to acquire quantitative data in Single Ion Monitoring (SIM) mode.

The correlation between methionine produced in green leaves, resulting from threonine synthase silencing, and chemical compounds found in cured tobacco has been monitored in cured leaves using LC-MS using the replicate lines described above. The extraction was performed in methanol. The equipment used is a Waters Acquity UPLC system coupled to MS. The column was a WatersXBridge Shield RP18 using as mobile phase A water:acetonitrile (95:5 v/v) and as mobile phase B methanol. The results are presented in Table 1.

As shown in Table 1, NtTS-RNAi plants did not show any visual differences from the control plants. For example, the plant height and chlorophyll content in the threonine synthase-silenced tobacco plants was almost identical to the control plants. The free methionine concentration in green leaves of the threonine synthase-silenced tobacco plants were higher than in the control plants. The methional concentration in aerosol was much higher in the threonine synthase-silenced tobacco plants than in the control plants. The threonine content of green leaves exhibited a reduction of more than 20% in the threonine synthase-silenced tobacco plants in comparison with the control plants.

Example 6

Analysis of Threonine Synthase Expression in NtTS-RNAi Tobacco Lines

SEQ ID NOs: 1, 2, 3 and 20 are aligned on a consensus of 1587 bases from the start to the stop codon. The fragment regions that are homologous between SEQ ID NOs: 1, 2 and 3 and different from SEQ ID NO:20 are nucleotides 1-46 of SEQ ID NOs: 1, 2 and 3 and nucleotides 1-52 of SEQ ID NO:20; nucleotides 99-141 of SEQ ID NO:1, nucleotides 102-144 of SEQ ID NO: 2 and SEQ ID NO:3 and nucleotides 102-153 of SEQ ID NO:20; and nucleotides 1325-1362 of SEQ ID NOs: 1, 2 and 3 and nucleotides 1334-1371 of SEQ ID NO:20. These sequences are used to design primers specific for SEQ ID NOs 1, 2, 3. A set of primers specific for SEQ ID NO: 20 are also designed.

NtTS-RNAi lines are prepared using regions corresponding to nucleotides 454-805 of SEQ ID NO:1; nucleotides 454-805 of SEQ ID NO: 2: nucleotides 456-805 of SEQ ID NO:3 and nucleotides 463-814 of SEQ ID NO:20. 3 individual plants from 3 independent NtTS-RNAi lines (NtTS1, NtTS2 and NtTS3), positively expressing the transgene(s) for RNAi silencing (tested by PCR for the presence of the $^{35}$S promoter in gDNA) are subjected to semi-quantitative RT-PCR using the primers specific for SEQ ID NOs: 1, 2 and 3 and primers specific for SEQ ID NO: 20. Tubulin is used as a control for the expression of house-keeping genes. 3 Burley TN90 plants are used as a control for the expression of the transcripts related to SEQ ID NOS: 1, 2, 3 and 20.

Using primers specific for SEQ ID NOS: 1, 2 and 3, or primers specific for SEQ ID NO: 3 only, or primers specific for SEQ ID NOS: 1 and 2 only in semi-quantitative RT-PCR indicates that a partial silencing in threonine synthase expression has occurred in each of the 3 independent NtTS-RNAi lines as compared to the control. Using primers specific for SEQ ID NO: 20 indicates that partial silencing in the NtTS-RNAi plants has occurred and that the level of silencing is less than that achieved for SEQ ID NOS: 1-3. Silencing was observed to be more effective for SEQ ID NO:3 than for SEQ ID NO:20, although the % sequence identity between the sequences is identical.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference.

Various modifications and variations of the disclosure will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 1

|  | CGS over expression | TN90 | VC | NtTS-RNAi line |
|---|---|---|---|---|
| Stalk height (cm) | 127 | 121 | 137 | 123 |
| Chlorophyllcontent (arbitrary unit) | 17 | 18 | 17 | 18 |
| Free methionine concentration in green leaves (mg/g) | Line 1: 0.025 (0.008) Line 2: 0.022 (0.016) | 0.025 (0.004) (average) | 0.017 (0.003) (average) | Line 1: 0.032 (0.013) Line 2: 0.034 (0.006) |
| Free threonine concentration in green leaves (mg/g) | Line 1: 0.876 (0.221) Line 2: 1.091 (0.087) | 0.851 (0.053) | 0.915 (0.110) | Line 1: 0.567 (0.051) Line 2: 0.609 (0.022) |
| Methional concentration in aerosol (μg/g) | na | 916 | 1400 | Line 1: 3822 Line 2: 2200 |

SEQUENCES

SEQ ID NO: 1 (DNA sequence of threonine synthase from N. tabacum)
atggcggcttcttcatgctcagatcttctttcctctctcctccttgttcccaactccatcaccaatcccttccaa atctaatcacattattcacttcattaatccaatcaaagccaccgcctctacaaatgacgcaattgtccctcccaaa agcaccgccgcccgccgacgaaaacatccgcgaagaggcggcgcgccgccgcacctcctcccacaatttctccgcc aggtacgttccttcaatgccgatcccagctccgacgaatggtattctcccgatgaaattatataccggagccgctc cggtggattacttgatgttcagcatgatatggacgctctgaagaaatttgatggccagtattggcggtcactgtttg attcacgtgtcggtaagaccacgtggccgtacggttcaggcgtttggtctaaaaaggaatgggtcctacctgaaatc gacagcgatgatattgttagtgcttttgaaggaaactctaatctgttttgggctgagcgttttggcaaacagtttct aggcatgagtgacttatgggtaaaacactgtggaatcagccatacgggtagttttaaggatctgggtatgaccgttt tggtgagtcaagtgaaccggttaaggaaaatgcataaaccagttgtaggtgtgggctgtgcttccactggtgacacg tcagctgcattgtcagcttactgtgcatctgcggggattccatccattgtattttaccagcaaataagatatctat ggcgcagctggtacaaccaatagctaacggagcttttgtgttgagtattgacaccgattttgatggttgtatgcagt tgattcgcgaagtcactgcagagttgcctatttacttggcgaattcgttgaatagtttgaggttagaagggcaaaag actgcagcaattgagattttgcagcagtttgatggcaaagtacccgattgggtgatagtacctggagggaacttgcg taatatatgctttctataaaggttttatgatgtgcagagagttggggctagttgaccgtatccctaggcttgtgt gtgctcaagcagctaacgctaatccgctttacttgcattataaatccggttggaaagactttcaacccgtgaaggcg aacaccacatttgcatctgctatacagattggtgatccagtgtctatagatagagctgtttttgccctgaagaactg tgacgggatagtcgaggaggcaacggaggaggagttgatggatgctatggctcaggcagactcaactgggatgttca tttgcccgcacactggtgtggcattgactgccctgttcaagttgagaaacagtggagttattggaccaaatgataag actgtggttgtgagtacagcacatggattgaagcttactcaatcaaagattgattaccactcaaaggaaataaagga catggaatgtcggtttgctaacccacctgtggaagtgaaagcagattttggatcagtcatggatgttctcaagaaat atttgttgagcaaaaatgccaagcactga SEQ ID NO: 2 (DNA sequence of threonine synthase from *N. tabacum* (Hicks Broad Leaf) that is also present in *Nicotiana sylvestris*)
atggcggcttctttcatgctcagatcttctttcctctctcctccttctcccaactccatcaccaatccccttccaa atctaatcacactattcacttcatcaatccaatcaaagccaccgcctctacaaatgacgcaattatccctccccaca aacatcgtcgccccgccgacgaaaacatccgcgaagaggcggcgcgccggcccacctcctcccacaatttctccgcc aggtacgttcctttcaatgccgaccccagctccgacgaatggtattctctcgatgaaattatataccggagccgctc cggtggcttacttgatgttcagcatgatatggacgctctgaagaaatttgatggccagtattggcggtcactgtttg aCtcacgtgtcggtaagaccacgtggccgtacggttcaggcgtttggtctaaaaaggaatgggtcctacctgaaatc gatagtgatgatattgttagtgcttttgaaggaaactctaatctgttttgggctgagcgttttggtaaacagtttct aggcatgagtgacttatgggtaaaacactgtggaattagccatacaggtagttttaaggatctgggtatgaccgttt tggtgagtcaagtgaaccggttaaggaaaatgcataaaccggttgttggtgtgggctgtgcttccactggtgacacg tcagctgcattgtcagcttactgtgcatctgcggggattccatcgattgtattttttacctgcaaataagatatctat ggcgcagctggtacaaccgatagctaacggagcttttgtgttgagcattgacaccgattttgatggttgtatgcagt tgattcgtgaagtcactgctgagttgccaatttacttggcgaattctttgaatagtttgaggttagaagggcaaaag actgcagcaattgagattttgcagcagtttgattggcaagttcccgattgggtgatagttcctggaggtaacttggg taatatatgcgttctataaaggttttatgatgtgcaaagagttggggctcgttgatcgtatccctaggcttgtgt gtgctcaagcagctaacgctaatccgctttacttgcattataaatccggttggaaagactttcaacccgtgaaggcg aacaccacatttgcatctgctatacagattggtgacccagtgtctatagatagagctgtttttgccctgaagaactg tgacgggatagtggaggaggcaacggaggaggagttgatggatgctatggctcaggcagactcaactgggatgttca tttgcccgcacactggtgtggcattgactgccctgttcaagttgagaaacagtggagttatcgggccaaatgataag actgtggttgtgagtacagcacatggattgaagtttactcaatcaaagattgattaccactcaaaggaaataaagga catggaatgtcggtttgctaacccacctgtggaagtgaaagcagattttggatcagtcatggatgttctcaagaaat atttgttgagcaaaaatgccaagcactga SEQ ID NO: 3 (DNA sequence of threonine synthase from *N. tabacum* (Hicks Broad Leaf))
atggcggcttctttcatgctcagatcttctttcctctctcctccttctcccaactccatcaccaatctcctcctaa atccaatcccactattcacttcatcaatccaatcaaagccaccgcctctacaaatgacgcaattatccctccccaga aacaccgccgcctgccgacgaaaatatccgcgaagaggccgctcgccgccccacctcctcccacaatttctccgcc aggtacgtgccCttcaatgcggatccaagctccgatgaatggtattctctcgatgaaatcatctaccggagccgctc cggcggcctacttgatgttcaacatgatatggacgctttaaaaaagtttgacggtcagtactggaggtcactttttg attcacgtgtcgggaagacgacgtggccttacgggtcaggtgtttggtctaagaaggaatgggtcctacccgaaatc gatagtgatgatattgttagtgcttttgaaggaaactcaaatctttttgggctgagcgttttggcaaacagtttct aggcatgagtgatttatgggtaaaacactgtggaattagtcatacaggtagttttaaggatctaggtatgactgttt tggtgagtcaagtgaaccggttaaggaaaatgcataaaccggttgttggtgtgggctgtgcttccactggtgacacg tcagctgcattgtcagcttactgtgcatctgcggggattccatcgattgtattttttacctgcaaataagatatctat ggcgcagctggtacaaccgatagctaacggagcttttgtgttgagcattgacaccgattttgatggttgtatgcagt tgattcgtgaagtcactgctgagttgccaatttacttggcgaattcgttgaatagtttgaggttagaagggcaaaag actgcagcaattgagattttgcagcagtttgattggcaagttcccgattgggtgatagttcctggagggaacttggg -continued taatatatatgcgttctataaaggttttatgatgtgcaaagagttggggctcgttgatcgtatccctaggcttgtgt
gtgctcaagcagctaacgcgaatccgctttatttgcattataaatccggttggaaagactttcaacccgtgaaggcg
aacaccacatttgcatctgctatacagattggtgacccagtgtctatagatagagctgtttttgccctgaagaactg
tgacgggatagtggaggaggcaacagaggaggagttgatgcatgctatggctaaggcagactcgactgggatgttca
tttgcccgcacactggtgtggcattgactgccctgttcaacttgagaaacagtggagttatcggaccaaatgataag
accgtggttgtgagtacagcacatggattgaagtttactcsatcaaagattgattatcactcaaaggaaataaagga
catggaatgtcggtttgctaacccacctgtggaagtgaaaccagattttggatcagtcatggatgttctcaagaaat
atttgttgagcaaaaatgccaagcactga SEQ ID NO: 4 (Genomic DNA sequence of SEQ ID NO: 3)
cgcagctgctttaactattttcgacactccattaatggcggcttctttcatgctcagatcttctttcctctctcctc
cttctccccaactccatcaccaatctcctcctaaatccaatcccactattcacttcatcaatccaatcaaagccacc
gcctctacaaatgacgcaattatccctccccagaaacaccgccgccctgccgacgaaaatacccgcgaagaggccgc
tcgccgccccacctcctcccacaatttctccgccaggtatgtaggggaagatatactagcgaaatgaatagataata
agcaaaatgaaaatagtgggtctaaaattacaataatttactcattgctcatttatttaatgctgacatcaaaagt
gctgcgtatgtcactgcaggtacgtgcctttcaatgcggatccaagctccgatgaatggtattctctcgatgaaatc
atctaccggagccgctccggcggcctacttgatgttcaacatgatatggacgctttaaaaaagtttgacggtcagta
ctggaggtcacttttttgattcacgtgtcgggaagacgacgtggccttacgggtcaggtgtttggtctaagaaggaat
gggtcctacccgaaatcgatagtgatgatattgttagtgcttttgaaggaaactcaaatctttttgggctgagcgt
tttggcaaacagtttctaggcatgagtgatttatgggtaaaacactgtggaattagtcatacaggtagttttaagga
tctaggtatgactgttttggtgagtcaagtgaaccggttaaggaaaatgcataaaccggttgttggtgtgggctgtg
cttccactggtgacacgtcagctgcattgtcagcttactgtgcatctgcggggattccatcgattgtatttttacct
gcaaataagatatctatggcgcagctggtacaaccgatagctaacggagcttttgtgttgagcattgacaccgattt
tgatggttgtatgcagttgattcgtgaagtcactgctgagttgccaacttacttggcgaattcgttgaatagtttga
ggttagaagggcaaaagactgcagcaattgagattttgcagcagtttgattggcaagttcccgattgggtgatagtt
cctggagggaacttgggtaatatatatgcgttctataaaggttttatgatgtgcaaagagttggggctcgttgatcg
tatccctaggcttgtgtgtgctcaagcagctaacgcgaatccgctttatttgcattataaatccggttggaaagact
ttcaacccgtgaaggcgaacaccacatttgcatctgctatacagattggtgacccagtgtctatagatagagctgtt
tttgccctgaagaactgtgacgggatagtggaggacgcaacagaggaggagttgatggatgctatggctaaggcaga
ctcgactgggatgttcatttgcccgcacactggtgtggcattgactgccctgttcaagttgagaaacagtggagtta
tcggaccaaatgataagaccgtggttgtgagtacagcacatggattgaagtttactcaatcaaagattgattatcac
tcaaaggaaataaaggacatggaatgtcggtttgctaacccacctgtggaagtgaaagcagattttggatcagtcat
ggatgttctcaagaaatatttgttgagcaaaaatgccaagcactga SEQ ID NO: 5 (Genomic DNA sequence of threonine synthase from Nicotinia tomentosiformis)
cgcagctgctttaactattttcgacactccattaatggcggcttctttcat -continued

```
ctggaggtcacttttttgattcacgtgtcgggaagacgacgtggccttacgggtcaggtgtttggtctaagaaggaat gggtcctacccgaaatcgatagtgatgatattgttagtgcttttgaaggaaactcaaatcttttttgggctgagcgt tttggcaaacagtttctaggcatgagtgatttatgggtaaaacactgtggaattagtcatacaggtagttttaagga tctaggtatgactgttttggtgagtcaagtgaaccggttaaggaaaatgcataaaccggttgttggtgtgggctgtg cttccactggtgacacgtcagctgcattgtcagcttactgtgcatctgcggggattccatcgattgtattttacct gcaaataagatatctatggcgcagctggtacaaccgatagctaacggagcttttgtgttgagcattgacaccgattt tgatggttgtatgcagttgattcgtgaagtcactgctgagttgccaatttacttggcgaattcgttgaatagtttga ggttagaagggcaaaagactgcagcaattgagattttgcagcagtttgattggcaagtccccgattgggtgatagtt cctggagggaacttgggtaatatatatgcgttctataaaggttttatgatgtgcaaagagttggggctcgttgatcg tatccctaggcttgtgtgtgctcaagcagctaacgcgaatccgctttatttgcattataaatccggttggaaagact ttcaacccgtgaaggcgaacaccacatttgcatctgctatacagattggtgacccagtgtctatagatagagctgtt tttgccctgaagaactgtgacgggatagtggaggaggcaacagaggaggagttgatggatgctatggctcaggcaga ctcgactgggatgttcatttgcccgcacactggtgtggcattgactgccctgttcaagtcgagaaacagtggagtta tcggaccaaatgataagaccgtggttgtgagtacagcacatggattgaagtttactcaatcaaagattgattatcac tcaaaggaaataaaggacatgaatgtcggtttgctaacccacctgtggaagtgaaagcagattttggatcagtcat ggatgttctcaagaaatatttgttgagcaaaaatgccaagcactga SEQ ID NO: 6 (Translated sequence of SEQ ID NO: 1)
MAASFMLRSSFLSPPCSQLHHQSPSKSNHIIHFINPIKATASTNDAIVPPQKHRRPADENIREEAARRRTSSHNFSA

RYVPFNADPSSDEWYSLDEIIYRSRSGGLLDVQHDMDALKKFDGQYWRSLFDSRVGKTTWPYGSGVWSKKEWVLPEI

DSDDIVSAFEGNSNLFWAERFGKQFLGMSDLWVKHCGISHTGSFKDLGMTVLVSQVNRLRKMHKPVVGVGCASTGDT

SAALSAYCASAGIPSIVFLPANKISMAQLVQPIANGAFVLSIDTDFDGCMQLIREVTAELPIYLANSLNSLRLEGQK

TAAIEILQQFDGKVPDWVIVPGGNLGNIYAFYKGFMMCRELGLVDRIPRLVCAQAANANPLYLHYKSGWKDFQPVKA

NTTFASAIQIGDPVSIDRAVFALKNCDGIVEEATEEELMDAMAQADSTGMFICPHTGVALTALFKLRNSGVIGPNDK

TVVVSTAHGLKFTQSKIDYHSKEIKDMECRFANPPVEVKADFGSVMDVLKKYLLSKNAKH

SEQ ID NO: 7 (Translated sequence of SEQ ID NO: 2)
MAASFMLRSSFLSPPSPQLHHQSPSKSNHTIHFINPIKATASTNDAIIPPQKHRRPADENIREEAARRPTSSHNFSA

RYVPFNADPSSDEWYSLDEIIYRSRSGGLLDVQHDMDALKKFDGQYWRSLFDSRVGKTTWPYGSGVWSKKEWVLPEI

DSDDIVSAFEGNSNLFWAERFGKQFLGMSDLWVKHCGISHTGSFKDLGMTVLVSQVNRLRKMHKPVVGVGCASTGDT

SAALSAYCASAGIPSIVFLPANKISMAQLVQPIANGAFVLSIDTDFDGCMQLIREVTAELPIYLANSLNSLRLEGQK

TAAIEILQQFDWQVPDWVIVPGGNLGNIYAFYKGFMMCKELGLVDRIPRLVCAQAANANPLYLHYKSGWKDFQPVKA

NTTFASAIQIGDPVSIDRAVFALKNCDGIVEEATEEELMDAMAQADSTGMFICPHTGVALTALFKLRNSGVIGPNDK

TVVVSTAHGLKFTQSKIDYHSKEIKDMECRFANPPVEVKADFGSVMDVLKKYLLSKNAKH

SEQ ID NO: 8 (Translated sequence of SEQ ID NO: 3)
MAASFMLRSSFLSPPSPQLHHQSPPKSNPTIHFINPIKATASTNDAIIPPQKHRRPADENIREEAARRPTSSHNFSA

RYVPFNADPSSDEWYSLDEIIYRSRSGGLLDVQHDMDALKKFDGQYWRSLFDSRVGKTTWPYGSGVWSKKEWVLPEI

DSDDIVSAFEGNSNLFWAERFGKQFLGMSDLWVKHCGISHTGSFKDLGMTVLVSQVNRLRKMHKPVVGVGCASTGDT

SAALSAYCASAGIPSIVFLPANKISMAQLVQPIANGAFVLSIDTDFDGCMQLIREVTAELPIYLANSLNSLRLEGQK

TAAIEILQQFDWQVPDWVIVPGGNLGNIYAFYKGFMMCKELGLVDRIPRLVCAQAANANPLYLHYKSGWKDFQPVKA

NTTFASAIQIGDPVSIDRAVFALKNCDGIVEEATEEELMDAMAKADSTGMFICPHTGVALTALFKLRNSGVIGPNDK

TVVVSTAHGLKFTQSKIDYHSKEIKDMECRFANPPVEVKADFGSVMDVLKKYLLSKNAKH

SEQ ID NO: 9 (Primer)
ctgaaatcgacagcgatgata
```

-continued

SEQ ID NO: 10 (Primer)
caaccaatagctaacggagctt

SEQ ID NO: 11 (Primer)
gagcatcgtggaaaaagaagac

SEQ ID NO: 12 (Primer)
aagctccgttagctattggttg

SEQ ID MO: 13 (Primer)
ttgattcacgtgtcggtaagac

SEQ ID NO: 14 (RNAi sequence used to silence threonine synthase)
ctgaaatcgacagcgatgatattgttagtgcttttgaacgaaactctaatctgttttgggctgagcgttttggcaaa cagtttctaggcatgagtgacttatgggtaaaacactgtggaatcagccatacgggtagttttaaggatctgggtat gaccgttttggtgagtcaagtgaaccggttaaggaaaatgcataaaccagttgtaggtgtgggctgtgcttccactg gtgacacgtcagctgcattgtcagcttactgtgcatctccggggattccatccattgtatttttaccagcaaataag atatctatggcgcagctggtacaaccaatagctaacggagctt SEQ ID NO: 15 (RNAi sequence used to silence threonine synthase)
ctgaaatcgatagtgatgatattgttagtgcttttgaaggaaactctaatctgttttgggctgagcgttttggtaaa cagtttctaggcatgagtgacttatgggtaaaacactgtggaattagccatacaggtagttttaaggatctgggtat gaccgttttggtgagtcaagtgaaccggttaaggaaaatgcataaaccggttgttggtgtgggctgtgcttccactg gtgacacgtcagctgcattgtcagcttactgtgcatctgcggggattccatcgattgtatttttacctgcaaataag atatctatggcgcagctggtacaaccgatagctaacggagctt SEQ ID NO: 16 (RNAi sequence used to silence threonine synthase)
ccgaaatcgatagtgatgatattgttagtgcttttgaaggaaactcaaatctttttgggctgagcgttttggcaaa cagtttctaggcatgagtgatttatgggtaaaacactgtggaattagtcatacaggtagttttaaggatctaggtat gactgttttggtgagtcaagtgaaccggttaaggaaaatgcataaaccggttgttggtgtgggctgtgcttccactg gtgacacgtcagctgcattgtcagcttactgtgcatctgcggggattccatcgattgtatttttacctgcaaataag atatctatggcgcagctggtacaaccgatagctaacggagctt SEQ ID NO: 17 (RNAi sequence used to silence threonine synthase)
ccgaaatcgatagtgatgatattgttagtgcttttgaaggaaactcaaatctttttgggctgagcgttttggcaaa cagtttctaggcatgagtgatttatgggtaaaacactgtggaattagtcatacaggtagttttaaggatctaggtat gactgttttggtgagtcaagtgaaccggttaaggaaaatgcataaaccggttgttggtgtgggctgtgcttccactg gtgacacgtcagctgcattgtcagctcactgtgcatctgcggggattccatcgattgtatttttacctgcaaataag atatctatggcgcagctggtacaaccgatagctaacggagctt SEQ ID NO: 18 (RNAi sequence used to silence threonine synthase)
ccgaaatcgatagtgatgatattgttagtgcttttgaaggaaactcaaatctttttgggctgagcgttttggcaaa cagtttctaggcatgagtgatttatgggtaaaacactgtggaattagtcatacaggtagttttaaggatctaggtat gactgttttggtgagtcaagtgaaccggttaaggaaaatgcataaaccggttgttggtgtgggctgtgcttccactg gtgacacgtcagctgcattgtcagcttactgtgcatctgcggggattccatcgattgtatttttacctgcaaataag atatctatggcgcagctggtacaaccgatagctaacggagctt SEQ ID NO: 19 (RNAi sequence used to silence threonine synthase)
Ctgaaatcgatagtgatgatattgttagtgcttttgaaggaaactctaatctgttttgggctgagcgttttggtaaa cagtttctaggcatgagtgacttatgggtaaaacactgtggaattagccatacaggtagttttaaggatctgggtat gaccgttttggtgagtcaagtgaaccggttaaggaaaatgcataaaccggttgttggtgtgggctgtgcttccactg gtgacacgtcagctgcattgtcagcttactgtgcatctgcggggattccatcgattgtatttttacctgcaaataag atatctatggcgcagctggtacaaccgatagctaacggagctt SEQ ID NO: 20 (DNA sequence of a further threonine synthase from N. tabacum)
atggcggcttcttcaacttgcatgttcagatcctctttcttctctcccaatctccatccaaagcaacaatcccctgctaa atccaacggcgttcagttcttcactcctattaaagccacagcttcttctacagatgatgcaatctccgcatctacacaac ctcaaaaacaccgccgccctgctgacgagaacatccgtgaggacgcccgccgccacatctcttcccacaatttctctgcc aggtatgtgccttttaatgccgaccctaactccagtgagtggtcttctctcgacgagatcatttaccgcagccgctccgg tggtctacttgatgtccagcatgatatggacgctctcaagaagtttgatggccagtactggcgctccctgtttgattccc gggtgggcaagaccacttggccttatggttctggtgtttggtccaagaaggaatgggtcctacctgaaattgacagtgat gatattgtcagtgcttttgaaggaaattccaatctttttgggctgagcgtttcggcaaacagttccttggcatgagtga tttgtgggtcaaacattgtggaatcagccacactggtagctttaaggatctcggcatgactgtactggtgagtcaagtaa atcggttgcggaaaatgcataaaccagtcgtgggtgtcggctgtgcttccactggagacacgtcagctgcactgtcggct tactgcgcatctgcaggcatcccatcaattgtattcttacctgcaaataagatttctatggcgcaactggttcaaccaat agccaatgggcttttgtgttgagtcttgacactgattttgatcgatgcatgcagttgattcgcgaagtcacagctgagt tgcccatttacttggcaaattccttgaatagtttgaggctagagggcaaaagacggcagctatagagattctgcagcag tttgactgggaagttcctgactgggtgataattcctggtggaaacctgggcaatatatgcattttataaaggttttca aatgtgcaaggagctgggacttgttgatcgtatcccgagacttgtttgtgctcaagcagccaatgcaaatccgctttact tgcattataaatctggttggaaagaattcaaatctgtcaaggccaatacaacatttgcatctgctatacagattggcgac cctgtatccatcgacagggctgtttatgcactgaagaactccaacgggatagtggaggaggcaactgaggaagagttgat ggatgcgatggctcaggcagattcaactgggatgttcatatgccccacactggcgtggcattgacagcactatccaagc tgagaaagacggggttattaggccaactgacaggaccgtggttgtgagtacagctcatgggttgaagtttactcaatcc aaggctgattatcattcaaaagaaataaagaacatggaatgcccgtttgctaatccaccagtgcaggtgaaagcagactt tggatcagtcatggatgttctcaagaaatacctgttgagcaaaaattctaagttctaa SEQ ID NO: 21 (Translated sequence of SEQ ID NO: 21)
MAASSTCMFRSSFFSPNLHPKQQSPAKSNGVQFFTPIKATASSTDDAISASTQPQKHRRPADENIREEARRHISSHNFSA

RYVPFNADPNSSEWYSLDEIIYRSRSGGLLDVQHDMDALKKFDGQYWRSLFDSRVGKTTWPYGSGVWSKKEWVLPEIDSD

DIVSAFEGNSNLFWAERFGKQFLGMSDLWVKHCGISHTGSFKDLGMTVLVSQVNRLRKMHKPVVGVGCASTGDTSAALSA

YCASAGIPSIVFLPANKISMAQLVQPIANGAFVLSLDTDFDGCMQLIREVTAELPIYLANSLNSLRLEGQKTAAIEILQQ

FDWEVPDWVIIPGGNLGNIYAFYKGFQMCKELGLVDRIPRLVCAQAANANPLYHYKSGWKEFKSVKANTTFASAIQIGD

PVSIDRAVYALKNSNGIVEEATEEELMDAMAQADSTGMFICPHTGVALTALSKLRKTGVIRPTDRTVVVSTAHGLKFTQS

KVDYHSKEIKNMECRFANPPVQVKADFGSVMDVLKKYLLSKNSKF

The invention claimed is:

1. A method for increasing the concentration of free methionine in at least part of a tobacco plant, comprising:

(a) reducing the expression or activity of threonine synthase in the tobacco plant by introducing into the tobacco plant a polynucleotide that exhibits RNA interference activity against threonine synthase mRNA to generate a mutant, non-naturally occurring, or transgenic tobacco plant, wherein the threonine synthase comprises (i) a polynucleotide comprising a sequence encoding the threonine synthase and having at least 97% sequence identity to SEQ ID NO:1, SEQ ID NO:2, SEQ ID NO:3, SEQ ID NO:4, or SEQ ID NO:5;

(ii) a polypeptide encoded by any one of said polynucleotides set forth in (i); or (iii) a polypeptide having at least 99% sequence identity to SEQ ID NO:6, SEQ ID NO:7, OR SEQ ID NO:8;

(b) measuring the concentration of free methionine in at least a part of the mutant, non-naturally occurring or transgenic tobacco plant obtained in step (a); and (c) identifying a mutant, non-naturally occurring or transgenic tobacco plant in which the concentration of free methionine therein has increased by at least 50% in comparison to a control tobacco plant in which the polynucleotide or polypeptide in step (a) is not introduced and wherein the visual appearance of said mutant, non-naturally occurring or transgenic tobacco plant is substantially the same as the control tobacco plant three months after field transplant or 36 days after topping.

2. A mutant, non-naturally occurring or transgenic tobacco plant or plant material that is obtained or obtainable by the method according to claim 1.

3. A mutant, non-naturally occurring or transgenic tobacco plant according to claim 2, wherein expression of threonine synthase or the activity of the protein encoded thereby is reduced and a part of the tobacco plant has an increase in methionine content of at least 50% as compared to a control tobacco plant in which the expression or the activity of threonine synthase has not been reduced and wherein the methional concentration in aerosol is increased by at least 5% as compared to the aerosol from the control tobacco plant.

4. The mutant, non-naturally occurring or transgenic tobacco plant according to claim 3, wherein the free threonine concentration in part of the tobacco plant is decreased as compared to the control tobacco plant.

5. Seed comprising cells or tissue from the tobacco plant of claim 2.

6. A tobacco product comprising a part of the tobacco plant of claim 2.

7. A method for producing methional comprising the steps of:
 (a) providing part of a tobacco product according to claim 6; and
 (b) providing heat thereto.

8. A tobacco product comprising a part of the tobacco plant of claim 3.

9. A method for producing methional comprising the steps of:
 (a) providing part of a tobacco product according to claim 8; and
 (b) providing heat thereto.

10. A tobacco product comprising a part of the tobacco plant of claim 4.

11. A method for producing methional comprising the steps of:
 (a) providing part of a tobacco product according to claim 10; and
 (b) providing heat thereto.

12. The mutant, non-naturally occurring or transgenic tobacco plant of claim 4, wherein (i) the free methionine concentration in leaves is at least about 0.03 mg/g; (ii) the free threonine concentration in leaves is at least about 0.5 mg/g; and (iii) the methional concentration in aerosol upon heating is at least about 2000 µg/g.

13. A method comprising:
 (a) introducing into a tobacco plant a polynucleotide that exhibits RNA interference activity against threonine synthase mRNA to generate a mutant, non-naturally occurring, or transgenic tobacco plant, wherein the threonine synthase mRNA
  (i) is transcribed from a polynucleotide having at least 97% sequence identity to SEQ ID NO:1, SEQ ID NO:2, SEQ ID NO:3, SEQ ID NO:4, or SEQ ID NO:5; or
  (ii) is translated into a polypeptide having at least 99% sequence identity to SEQ ID NO:6, SEQ ID NO:7, OR SEQ ID NO:8;
 (b) measuring the concentration of free methionine in at least a part of the mutant, non-naturally occurring or transgenic tobacco plant obtained in step (a); and
 (c) identifying a mutant, non-naturally occurring or transgenic tobacco plant in which the concentration of free methionine therein has increased by at least 50% in comparison to a control tobacco plant in which the polynucleotide or polypeptide in step (a) is not introduced and wherein the visual appearance of said mutant, non-naturally occurring or transgenic tobacco plant is substantially the same as the control tobacco plant three months after field transplant or 36 days after topping.

14. A method comprising:
 (a) generating a mutant, non-naturally occurring, or transgenic tobacco plant by introducing into a tobacco plant a polynucleotide encoding RNA that
  (i) has at least 97% sequence identity to mRNA transcribed from a polynucleotide comprising a sequence of SEQ ID NO:1, SEQ ID NO:2, SEQ ID NO:3, SEQ ID NO:4, or SEQ ID NO:5, or
  (ii) has at least 99% sequence identity to mRNA that is translated into a polypeptide comprising an amino acid sequence of SEQ ID NO:6, SEQ ID NO:7, OR SEQ ID NO:8;
 (b) measuring the concentration of free methionine in at least a part of the mutant, non-naturally occurring or transgenic tobacco plant of step (a); and
 (c) identifying a mutant, non-naturally occurring or transgenic tobacco plant in which the concentration of free methionine therein has increased by at least 50% in comparison to a control tobacco plant in which the polynucleotide or polypeptide in step (a) is not introduced and wherein the visual appearance of said mutant, non-naturally occurring or transgenic tobacco plant is substantially the same as the control tobacco plant three months after field transplant or 36 days after topping.

15. The method of claim 14, wherein the polynucleotide introduced into the tobacco plant in step (a) encodes RNA having at least 10 nucleotides.

16. The method of claim 14, wherein the polynucleotide introduced into the tobacco plant in step (a) encodes double stranded RNA.

* * * * *